US007988850B2

(12) United States Patent
Roncadi et al.

(10) Patent No.: US 7,988,850 B2
(45) Date of Patent: Aug. 2, 2011

(54) MEDICAL APPARATUS WITH IMPROVED USER INTERFACE

(75) Inventors: Fabio Roncadi, Mirandola (IT); Marco Salsa, Cameri (IT); Matteo Malagoli, Carpi (IT); Glenn Sanders, Larkspur, CO (US); Gary Warns, Arvada, CO (US)

(73) Assignee: Gambro Lundia AB (SE)

( * ) Notice: Subject to any disclaimer, the term of this patent is extended or adjusted under 35 U.S.C. 154(b) by 1260 days.

(21) Appl. No.: 11/640,919

(22) Filed: Dec. 19, 2006

(65) Prior Publication Data

US 2007/0138069 A1 Jun. 21, 2007

Related U.S. Application Data

(60) Provisional application No. 60/751,214, filed on Dec. 19, 2005.

(51) Int. Cl.
*A61M 1/14* (2006.01)
(52) U.S. Cl. .................. 210/96.2; 210/321.65; 210/929; 345/440; 702/85; 700/32; 700/83
(58) Field of Classification Search .............. 700/83, 700/28, 32; 210/646, 96.2, 321.65, 929; 345/440; 702/85
See application file for complete search history.

(56) References Cited

U.S. PATENT DOCUMENTS

| 5,247,434 | A | 9/1993 | Peterson et al. |
| 5,326,476 | A | 7/1994 | Grogan et al. |
| 5,546,582 | A | 8/1996 | Brockmeyer et al. |
| 5,788,851 | A | 8/1998 | Kenley et al. |
| 6,830,693 | B2 | 12/2004 | Govoni et al. |
| 6,881,344 | B2 | 4/2005 | Vasta et al. |
| 2003/0018395 | A1 | 1/2003 | Crnkovich et al. |

FOREIGN PATENT DOCUMENTS

| WO | WO94/11093 | 5/1994 |
| WO | WO02/07796 A1 | 1/2002 |

OTHER PUBLICATIONS

International Search Report for International Application No. PCT/IB2006/000203, (Aug. 2006).

*Primary Examiner* — Terry K Cecil
(74) *Attorney, Agent, or Firm* — Finnegan, Henderson, Farabow, Garrett & Dunner, LLP

(57) ABSTRACT

A medical apparatus comprises a control system allowing storage of a number of shaping profiles. Each shaping profile is stored as a plurality of pairs, including a shaping profile reference value and a time interval value. The reference value is represented as fraction, for instance a percentage, of the total weight loss the apparatus should achieve at the end of a treatment time. Each time interval value is represented either as fraction of the total treatment time or as a prefixed actual time interval. The control system calculates the actual weight loss rate versus time profile based on the desired total weight loss, on the desired total treatment time as well as on selected desired shaping profile.

51 Claims, 12 Drawing Sheets

MEDICAL APPARATUS WITH IMPROVED USER INTERFACE

CROSS REFERENCE TO RELATED APPLICATIONS

This application claims the benefit of U.S. Provisional Application No. 60/751,214, filed on Dec. 19, 2005 which is incorporated by reference.

TECHNICAL FIELD

The invention relates to a medical apparatus with improved user interface. The medical apparatus of the invention could be an apparatus intended for the extracorporeal treatment of blood, for instance by hemodialysis, hemofiltration, hemodialfitration, ultrafiltration, plasmapheresis or an apparatus for processing whole blood and/or blood components.

BACKGROUND ART

Blood treatment apparatus and similar medical devices comprise an extracorporeal circuit provided with at least one blood treatment or blood processing unit, one tube, connecting a blood removal zone to said unit, and a second tube, extending downstream of the treatment or processing unit towards a blood return zone to the patient or towards a blood/blood components collection zone. Blood is moved from the patient or donor to the treatment or processing unit via pumps or other actuators controlled by the machine.

In case the machine is for instance a hemodialysis apparatus, then for achieving the required treatment of blood, an adequately prepared dialysis liquid shall be sent to the treatment unit, and water removal through the treatment unit membrane as well other machine parameters shall be controlled. Depending upon the type of hemodialysis machine and upon the type of treatment, a user can have the possibility to set a number of parameters in order to impose a specific prescription to a patient, such as for instance: flow rates of the various liquids, temperatures and conductivity of the liquids, concentration of the liquids used during treatment, flow rates of any anticoagulants used and delivered during treatment, pressures in the fluid conduits, net liquid removal rates of plasma water from whole blood and so on.

It is therefore evident that users (the patient himself, a physician, a nurse) have normally a plurality of parameters to set before or even during the process performed by the medical apparatus.

Particularly important parameter are those that can take variable values or profiles through the treatment, referring to extracorporeal blood treatment these parameters can be ultrafiltration, conductivity of the dialysis liquid, concentration of a specific substance in the dialysis liquid, flow rate of an infusion or substitution solution, temperature of the dialysis liquid, temperature of blood, temperature of an infusion solution, concentration of a certain specific drug that is delivered to the patient, etcetera.

In this situation it is important that machines as blood treatment machines or blood processing apparatus where the process executed by the machine acts on a patient's or donor's blood, the user interface is designed to allow easy and safe data entry.

Particularly, in case of treatment of patients suffering from kidney failure, the patient is constantly connected to the machine with the serious risk that any failure in entering or in actuating a prescription could have negative impacts on the treatment delivery and on patient's health.

In this situation several technical solutions have been developed in the past in order to render parameters values data entry in blood treatment or blood processing apparatus relatively easy and reliable.

A data entry user interlace of general purpose and not specifically designed for the medical field is known from U.S. Pat. No. 5,546,582.

A first known method for entering data in a dialysis machine is described in U.S. Pat. No. 5,247,434. This method comprises the following steps:

(a) providing a touch screen interface with an indicium thereon corresponding to a treatment parameter;
(b) touching the indicium;
(c) in response to said touching, invoking a data entry pad on a region of the touch screen,
(d) entering a parametric value corresponding to the treatment parameter by touching one or more buttons of the data entry pad;
(e) touching a first region of the data entry pad to signal entry of the parametric value;
(f) displaying on the touch screen a button soliciting verification of the newly entered parametric value;
(g) touching the button soliciting verification; and
(h) in response to steps (b)-(g), causing the parametric value corresponding to the treatment parameter to be changed.

In other words before really implementing a change a user is solicited to verify the newly entered parameter and to press a button confirming the change.

The same patent also discloses a method for entering variable parameters, i.e. parameters that can vary in the course of time during treatment.

More in detail U.S. Pat. No. 5,247,434 shows a method of programming a time-varying parameter comprising the steps:

(a) providing a touch screen interface;
(b) displaying on the touch screen first and second axes, the first axis corresponding to the time-varying parameter, the second axis corresponding to time;
(c) touching the touch screen at a plurality of points to define points on a parameter-versus-time curve;
(d) presenting on the touch screen a series of bars corresponding to said curve;
(e) selecting one of said bars for alteration;
(f) displaying on the screen a numeric parameter corresponding to the selected bar;
(g) touching the screen at first or second locations to increase or decrease, respectively, the displayed numeric parameter and thereby alter the value of the numeric parameter to which the selected bar corresponds.
(h) touching the screen at a third location to signify completion of steps (b)-(g), and
(i) storing data corresponding to the bars in a memory to which the process-control system can refer in changing the time-varying parameter with time.

Document U.S. Pat. No. 5,326,476 teaches a further method for entering a time variable parameter, ultrafiltration in particular, in a hemodialysis machine, having a programmable memory and having ultrafiltration capability, so as to enable the machine to perform ultrafiltration of fluid from a patient according to a time-variable ultrafiltration profile. The method disclosed in U.S. Pat. No. 5,326,476 comprises the following steps:

(a) entering into the programmable memory a prescribed time for dialysis;
(b) entering into the programmable memory a target ultrafiltration volume of fluid to be removed from the patient;

(c) entering into the programmable memory a proposed ultrafiltration profile being representable as a plot of coordinates on an ultrafiltration rate axis and a time axis and defining a profile ultrafiltration volume; and (d) shifting the proposed ultrafiltration profile along the ultrafiltration rate axis to the degree necessary to make the profile ultrafiltration volume equal to the target ultrafiltration volume, so as to allow the hemodialysis machine to achieve, while ultrafiltrating the fluid according to the shifted ultrafiltration profile, the entered target ultrafiltration volume within the entered prescribed time.

This method allows the user to enter a profile curve and to move the ultrafiltration profile along the ordinates so as to achieve the desired integral value in the desired time frame.

A further user interface system for a dialysis machine is known from document U.S. Pat. No. 5,788,851. This user interface does not specifically relate to data entry of profiles and comprises, in summary, the following features:
  a touch screen displaying messages and information and permitting to select a parametric value pertinent to operation of said machine or pertinent to a treatment by said machine,
  one hard key off of said touch screen, said touch screen prompting a user to press said hard key to signify that the selection of the parametric value has been completed;
  a control system having a host and a safety processing unit, wherein pressing of said hard key causes transfer of information relating to the selected parametric value from the host processing unit to the safety processing unit which is then checking said selected parametric value to confirm that said parametric value meets validation or safety criteria for a patient connected to said machine.

A further known technique is described in U.S. Pat. No. 6,830,693, which relates to a method of setting up a dialysis treatment in a dialysis machine comprising the steps of: determining conditions of a dialysis treatment adapted to a specific patient, determining a first function (U(t)) of a first quantity (U) characterizing the dialysis treatment as a function of time (t) the first function (U(t)) satisfying said conditions of the dialysis treatment and corresponding to a curve having a defined shape; and determining a second function (C(t)) of a second quantity (C) characterizing the dialysis treatment, the second function (C(t)) being correlated with the first function (U(t)) by constants (M, N) determined experimentally and the second function (C(t)) corresponding to a curve having a shape of the same kind as the shape of the first curve.

Finally, U.S. Pat. No. 6,881,344 relates to a user interface and to a method of setting up a dialysis treatment in a dialysis machine wherein a group of parametric functions (U(t, P); C(t, P)) representing ultrafiltration or conductivity as a function of time (t) and of a parameter (P) are provided. By imposing boundary conditions that are characteristic of a particular therapy and assigning values to the parameter (P) the user selects the curve and the machine calculates and displays the curves corresponding to the user's selection; the user can then confirm selection on the basis of the images of the curves.

SUMMARY OF THE INVENTION

While the above disclosed systems and methods served to give the user possibility to enter data in a relatively easy manner and/or served to reduce data entry errors, the present invention aims to further improve ease and reliability in data entry and visualization procedures for medical devices and particularly for blood treatment or blood processing machines wherein parameters variable in the course of a session need to be programmed.

In particular the invention aims to reduce as possible the efforts for the user to configure, modify and execute settings relating to variable parameters.

Moreover, the invention aims to render quick and intuitive creation and modification of profiles relating to variable parameters.

Furthermore the invention aims to offer an efficient use of the memory resources of the system without Impairing on usability.

Moreover, when for instance applied to the blood treatment area, the invention avoids to enter a reference profile that has to be stored, analyzed to determine which cumulative value (total weight loss if the profile is a weight loss rate profile) generates across a reference treatment time and then adapted to fit a desired cumulative value. By virtue of the features of the invention the profile of a certain parameter is calculated by the inventive solution to directly and immediately fit the desired cumulative value.

The above aims are reached by a medical apparatus and by a user interface according the invention. Further characteristics and advantages will better emerge from the following description in relation to some preferred but non-exclusive embodiments of an apparatus according to the invention.

SHORT DESCRIPTION OF THE DRAWINGS

The description will be made with reference to the figures of the accompanying drawings, provided by way of non-limiting example, in which:

FIG. 1 is a schematic representation of a medical apparatus for instance a blood treatment machine, according to the invention;

FIG. 2 to a user interface of the apparatus of the invention during delivery of a dialysis treatment;

DETAILED DESCRIPTION

Figure 1:
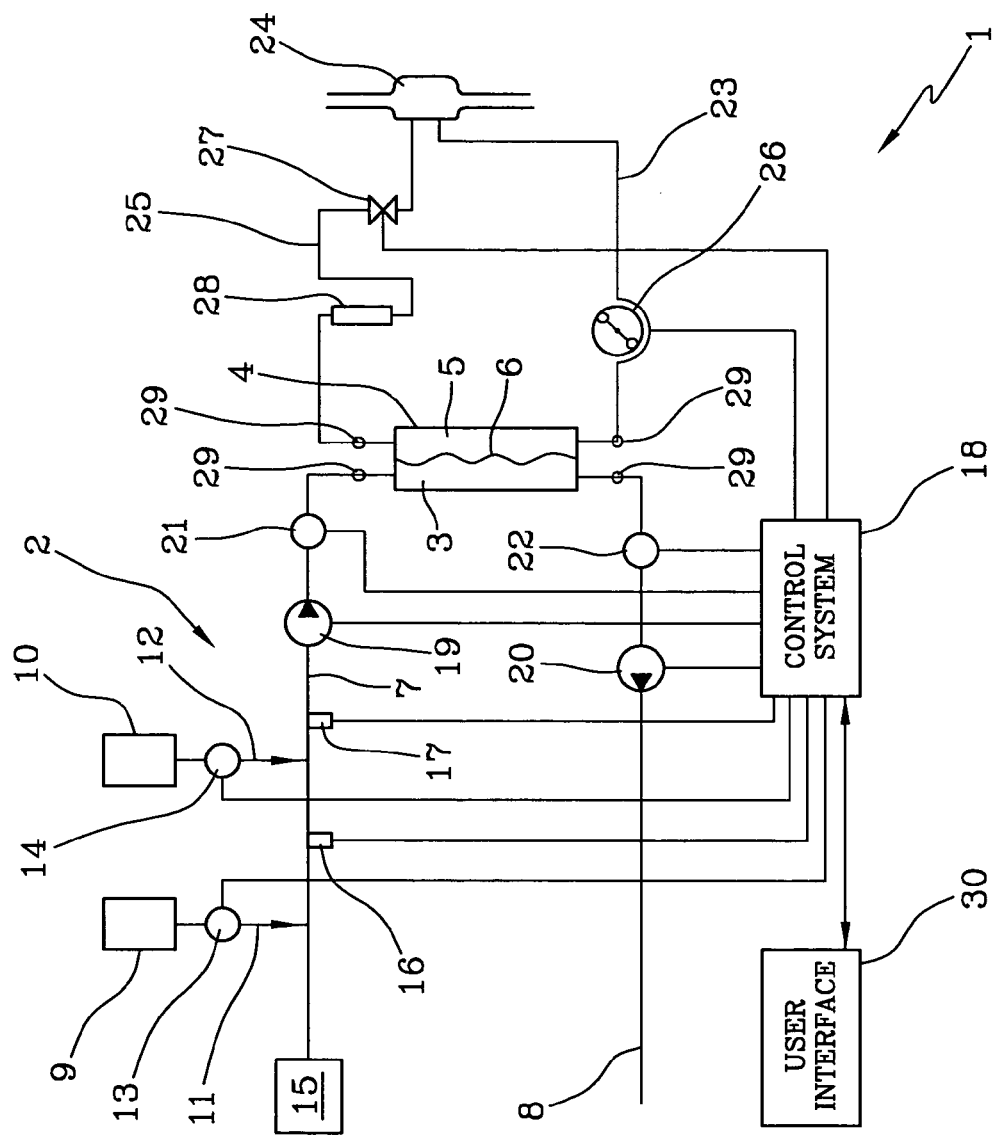

With reference to the figures, reference number I denotes a medical apparatus. The medical apparatus of the shown embodiment is a machine for the extracorporeal treatment of blood. Of course the medical apparatus of the invention could alternatively be a blood processing device or a blood component preparation device or other medical apparatus for fluid delivery/collection.

The apparatus shown in the enclosed drawings comprises a module 2 for preparing dialysis liquid to be sent into a first chamber 3 of a blood treatment unit 4, which is formed by a casing defining at least two chambers 3, 5 separated by a semipermeable membrane 6. The dialysis preparation module 2 includes tubing 7 bringing dialysis liquid to the first chamber inlet, while a waste line 8 receives spent liquid exiting via an outlet of the first chamber. In detail, the module 2 includes one or more concentrate containers 9, 10 delivering concentrated solutions, via respective lines 11, 12 and upon the action of respective concentrate pumps 13, 14, into the tubing 7 thereby properly mixing water coming from a source 15 with said concentrates and obtaining the dialysis liquid. Conductivity or concentration sensors 16, 17 can be provided on tubing 7 downstream each respective concentrate line. Said sensors provide control signals to a control system 18 which is responsible to then act on the concentrate pumps. Notice that sensors (not shown) detecting conductivity or concentration of electrolytes can also be present on the return-tubing 8 containing waste liquid. A pump 19 is generally operating on tubing 7 and a pump 20 on the waste line 8. Of course different alternative embodiments can be envisaged to bring dialysis liquid to the treatment unit with appropriate chemical and physical properties. For instance pre-prepared dialysis liquid bags could be used with no need of online preparation of dialysis liquid starting from concentrates and water. Fluid balance sensors, for instance a first and a second flow-meter 21, 22, operating on tubing 7 and on waste line 8 respectively, are used and are connected to the control system to provide signals necessary for regulating at least one of pumps 19, 20. Of course other fluid balance systems can be used: scales for instance or balance chambers or any other volumetric or mass or flow-rate based system available to the skilled man.

When the apparatus is in use, an extracorporeal blood circuit is connected to the second chamber 5. The extracorporeal circuit usually comprises at least an access branch 23 extending between a blood removal zone 24 from a patient or donor and the treatment unit 4, at least a return branch 25 extending downstream of the treatment unit, between the second chamber and a return zone of the blood to the patient; a peristaltic pump 26 is operatively associated to a length of pump tube of the extracorporeal circuit~ access branch. A clamp or other closure device 27 can operate on the blood return branch 25, typically downstream from a gas separator 28.

Usually, at the removal and return branches of the blood to or from the patient access means are provided to the cardiovascular system of the patient, for example constituted by needles of appropriate sizes, catheters or accesses of different types. One or more liquid infusion lines could be provided connected at one end to an infusion liquid source (a bag or in-line infusion liquid preparation system) and at the other end to, the extracorporeal circuit, or directly to the patient or donor.

Other sensors, such as pressure sensors 29, can be provided either on the extracorporeal circuit and/or on the dialysis liquid side of the apparatus. Furthermore sensors not herein disclosed in detail are provided with for directly or indirectly detecting the actual value of each machine or treatment parameter of interest, included those that can be set by the user, as it will appear from the following description.

The medical apparatus 1, described above, represents a non-limiting example, which the present invention can be applied to. The apparatus can include other components, which are not herein disclosed, as they are not relevant for the purpose of the understanding of present invention.

User Interface

The apparatus 1 presents at least a user interlace 30 for enabling setting of a plurality of parameters pertinent to operation of said apparatus or pertinent to a treatment to be performed by said apparatus. The parameters pertinent to the apparatus operation can be settings for one or more actuators (pumps, warmers, valves, etcetera depending upon the apparatus), while the parameters relating to the treatment performed by the apparatus can be settings on prescription parameters that have to be achieved (in case of blood treatment these settings can be fluid removal rate, total weight loss in the course of a treatment session, achievement of a desired concentration of a substance(s) in blood, etcetera). It should be noted that some parameters can assume values variable in the course of the same treatment or procedure. These parameters are herein referred to as profiles and can be set either before hand, or at the beginning of a treatment or even during the treatment (in this latter case it is clear that the setting will have no impact on the part of the treatment the apparatus has already delivered); referring to the extracorporeal blood treatment field, parameters which the operator could be interested to set can be the following: the rate of ultrafiltration in the course of a treatment (i.e. the amount of fluid per unit of time removed from blood through the membrane 6), the rate of infusion of a substance in the patient's or donor's blood, the conductivity or temperature or chemical concentration of a substance in a treatment liquid (for instance in the dialysis or in the infusion liquid), etcetera. The present invention is mainly focused to how these kind of variable parameters (or profiles) are stored in the medical apparatus control system, as well as to how these profiles, can be selected, modified, and actuated during a treatment session. While the user interface herein disclosed is connected with and part of the medical apparatus 1, it shall be understood that the user interface 30 could be manufactured and sold separately and then connected to a medical apparatus.

The user interface 30 of the embodiment shown includes a screen 31, for instance a touch screen, which allows interaction with the user interlace, for instance selection of certain parameters, visualization, either in analogical or in digital form, of values of said parameters and display of other information as it will be here below in detail described. Please note that the enclosed figures . . . show only the screen portion of the user interface 30, of course depending upon the case the user interface could include also buttons, knobs, or other hardware means positioned off the screen and operable to introduce entries into the control system. The activity of the user interface is determined by control system 18, which is connected to the user interface, is responsive to actions by a user on said user interface, and controls operations of the medical apparatus 1 by acting on a plurality of actuators (such as pumps 12, 13, 19, 20, 27, valve 27 and others) and by receiving signals by a plurality of sensors (such as for instance sensors 12, 13, 21, 22, 29 etc.).

The control system of presently shown embodiment includes a main control unit, connected to the user interface 30, and at least a memory connected to the main control unit. From a technical point of view the main control unit includes at least a microprocessor, while the above mentioned memory can be in a single physical memory or in physically separated memory devices.

For the purpose of practically explaining the present invention, a non-limiting example of a possible implementation of the features of the present invention is given here below with reference to an embodiment of a user interface. Of course the present invention features could be applied to user interfaces other than the one disclosed herein in detail.

Figure 2:
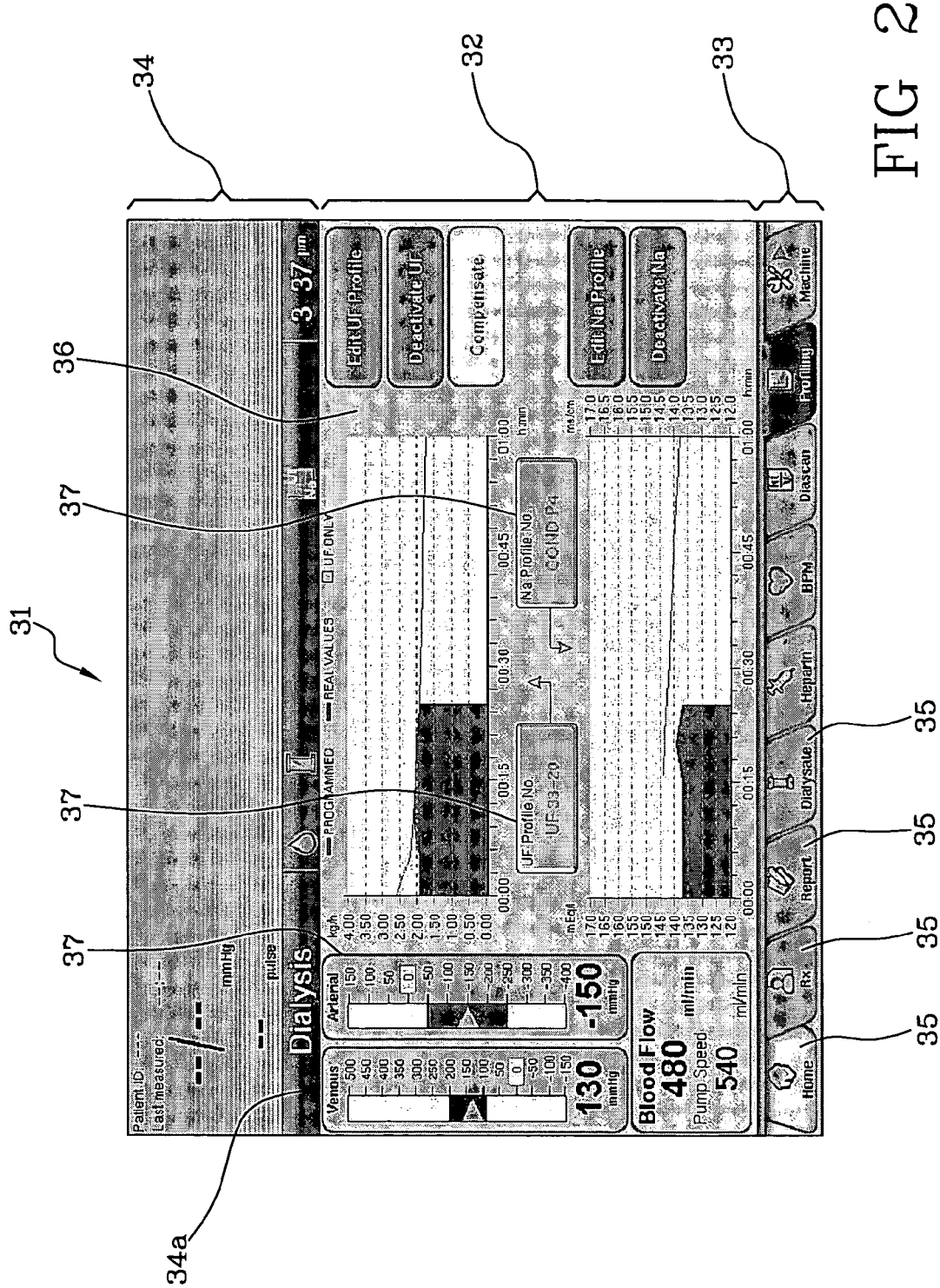

Referring to the enclosed features, the control system 18 is programmed (for instance by loading a program in the memory which then is executed by the CPU) for defining on screen 31 an operating region 32, where a number of working displays can be displayed, and a navigation region 33, where a number of navigation keys can be displayed (see FIG. 2). The working displays are shown one per time according to a sequence, which depends upon the sequence of activation of the navigation keys, as it will be apparent from below description.

The operating region 32 of the embodiment in FIG. 2 is adjacent to and in contact with the navigation region 33 and, in particular, is placed between the navigation region and a status bar region 34 extending transversally in the top part of the screen 31.

The navigation region of the non-limitative embodiments shown is in the bottom part of the screen and contains a plurality of navigation keys 35.

Of course the relative positions of regions 32, 33 and 34 could be differently arranged without departing from the scope of the invention. The control system displays in the working region a plurality of working displays 36, each including one or more indicia, such as touch buttons or touch icons 37, which can be selected to access particular submenus and/or for selecting a parameter or a group of parameters for successive modification of the value(s) thereof.

As the medical apparatus could work according to different operating modes (for instance by way of non-limiting example idle mode, setup mode, priming mode, treatment mode, and rinse-back mode), the user interface reflects said operating modes in the status region 34. This latter identifies in a band 34a, information relating to the operating mode, while the working region shows a plurality of working displays accessible to the user for entering commands or for modifying settings of one or more parameters (see FIGS. 2 and 3). Each working display 36 can also display information, in alphanumeric or in analogical or in graphic form, regarding the status of the machine, its operating conditions, the current actual values of one or more parameters, etcetera. When displayed according to the technique here below described, each working display occupies the entire operating region, overlapping to or hiding previously displayed working displays. The status bar in addition to information concerning the status mode of the machine (flushing, treatment, priming, rinse back, etc.) or can also provide alarm or information messages 34b (see FIG. 2).

The control system is programmed for associating each of said number of navigation keys 35 with a corresponding working display 36 so that each working display is selectable and displayable in the working region upon selection of the corresponding navigation key. The user can therefore navigate through the various menus and sub-menus of the working display by acting on the navigation keys and on buttons appearing in the working display.

The above-disclosed non-limiting example of a navigation logic controlled by the control system allows the user to enter data and parameter values into the apparatus memory. Parameters having values, which should change in the course of the treatment or in the course of an operation (i.e. profiles), can also be entered via user interface 30.

The apparatus of the enclosed embodiment comprises a control system programmed for allowing entry of profiles in one or more of the following circumstances:
  during apparatus configuration;
  during machine setup before starting a treatment;
  during delivery of a treatment.

Profiles Entry Management During Apparatus Configuration

In the following description, configuration is intended as the moment where the machine is neither running a treatment nor being submitted to preparation steps for running a treatment. Configuration is normally executed when installing the machine or periodically by technically qualified people when updating the machine configuration. The control system can be programmed to offer the operator to enter in configuration mode: access to configuration mode can be password protected as configuration should be a limited access environment for technically qualified personnel.

During configuration the control system is programmed for storing one or more shaping profiles shaping profiles are profiles, which are intended to represent the dynamic behavior taken by a first magnitude at the change of a second correlated magnitude. Shaping profile are not formed or defined by the actual values of a machine or patient parameters but are for instance non-dimensional or normalized representations of two correlated series of magnitudes. Each shaping profile is stored in the control system memory as a plurality of pairs 39, 40, each pair including a reference value 39 and a respective time interval value 40.

Figure 3:
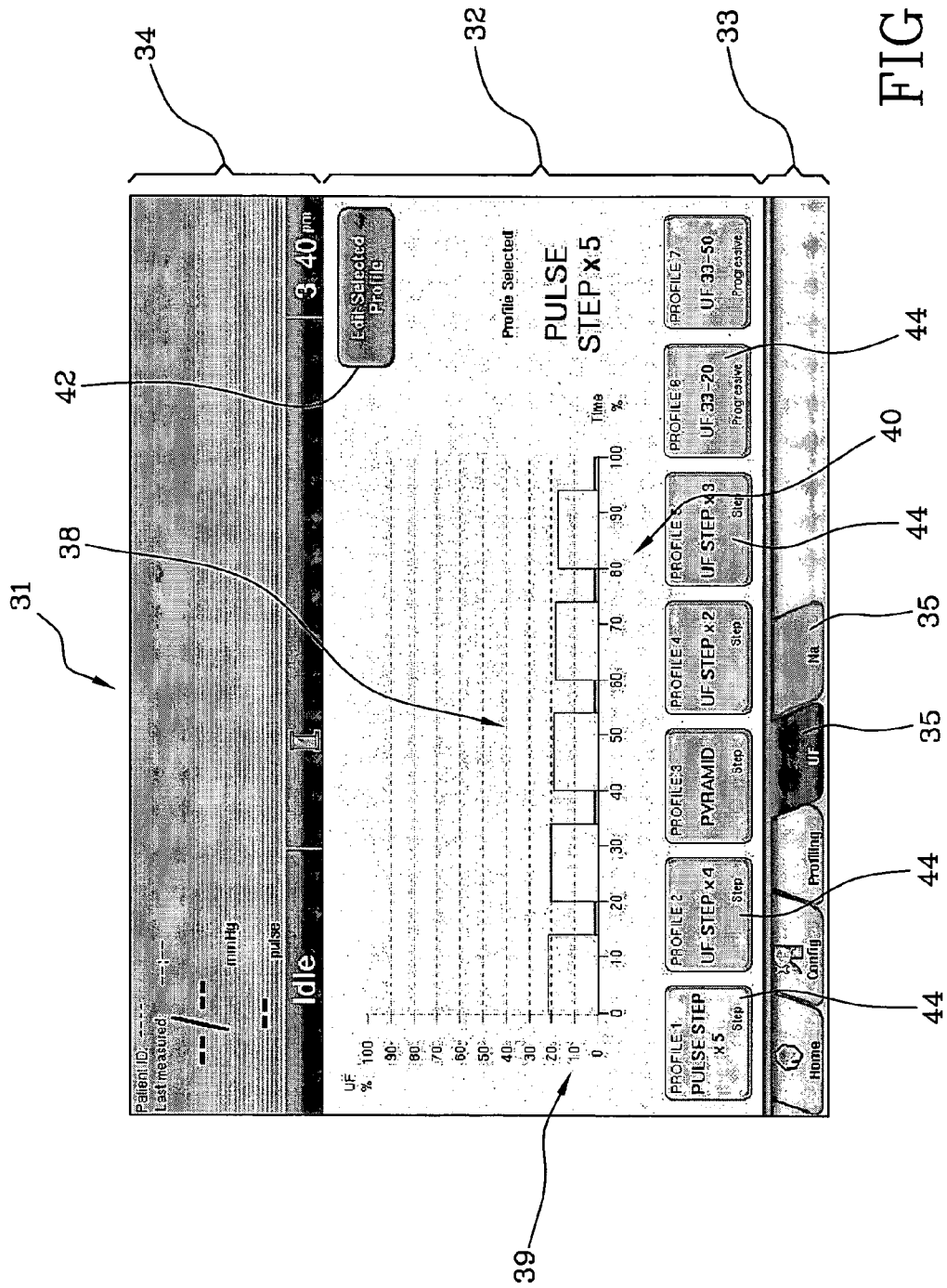
FIGS. 3 to 7 and 12 show a user interface according to the invention during the medical apparatus configuration.

Each time interval value can be a fraction of the total treatment time (for instance expressed as a percentage of the total treatment time) or a prefixed time interval (for instance expressed as a certain amount of seconds), while each reference value is stored as a fraction of total weight loss to be removed by a patient during total treatment time. The embodiment of FIG. 3 shows a shaping profile 38 where percentages of a reference value 39 are correlated to corresponding percentages of time interval values 40.

Figure 4:
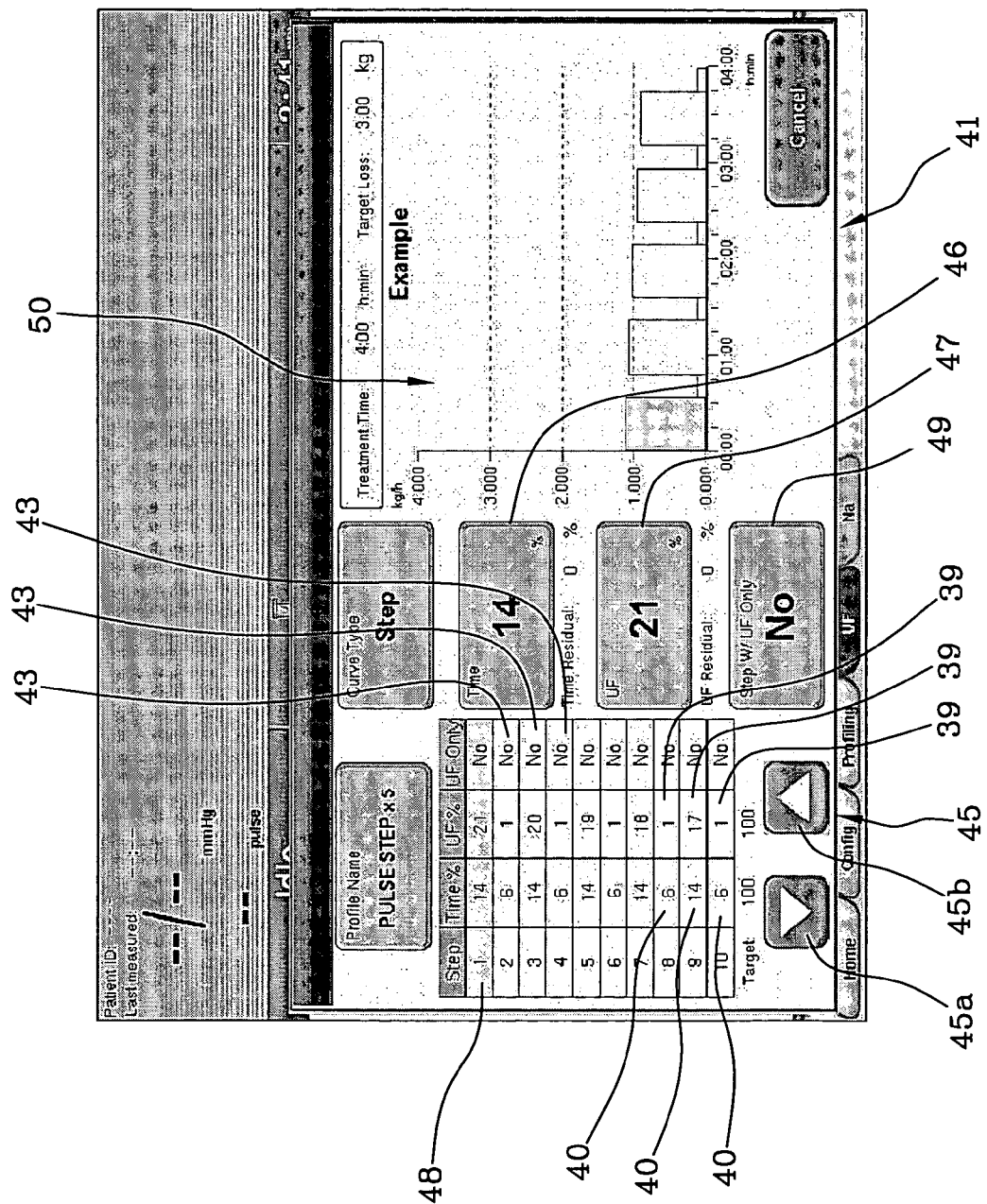
Figure 5:
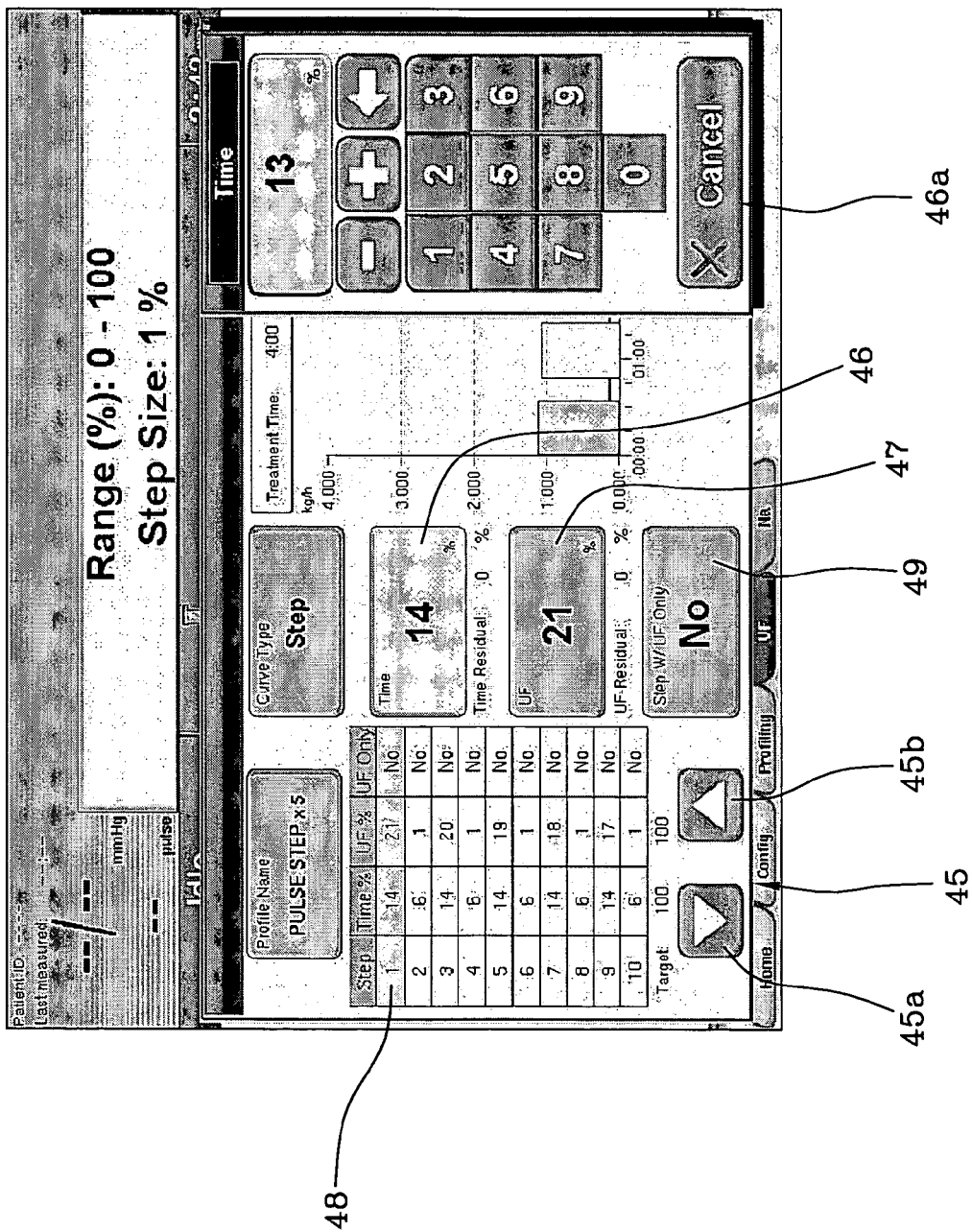
Figure 6:
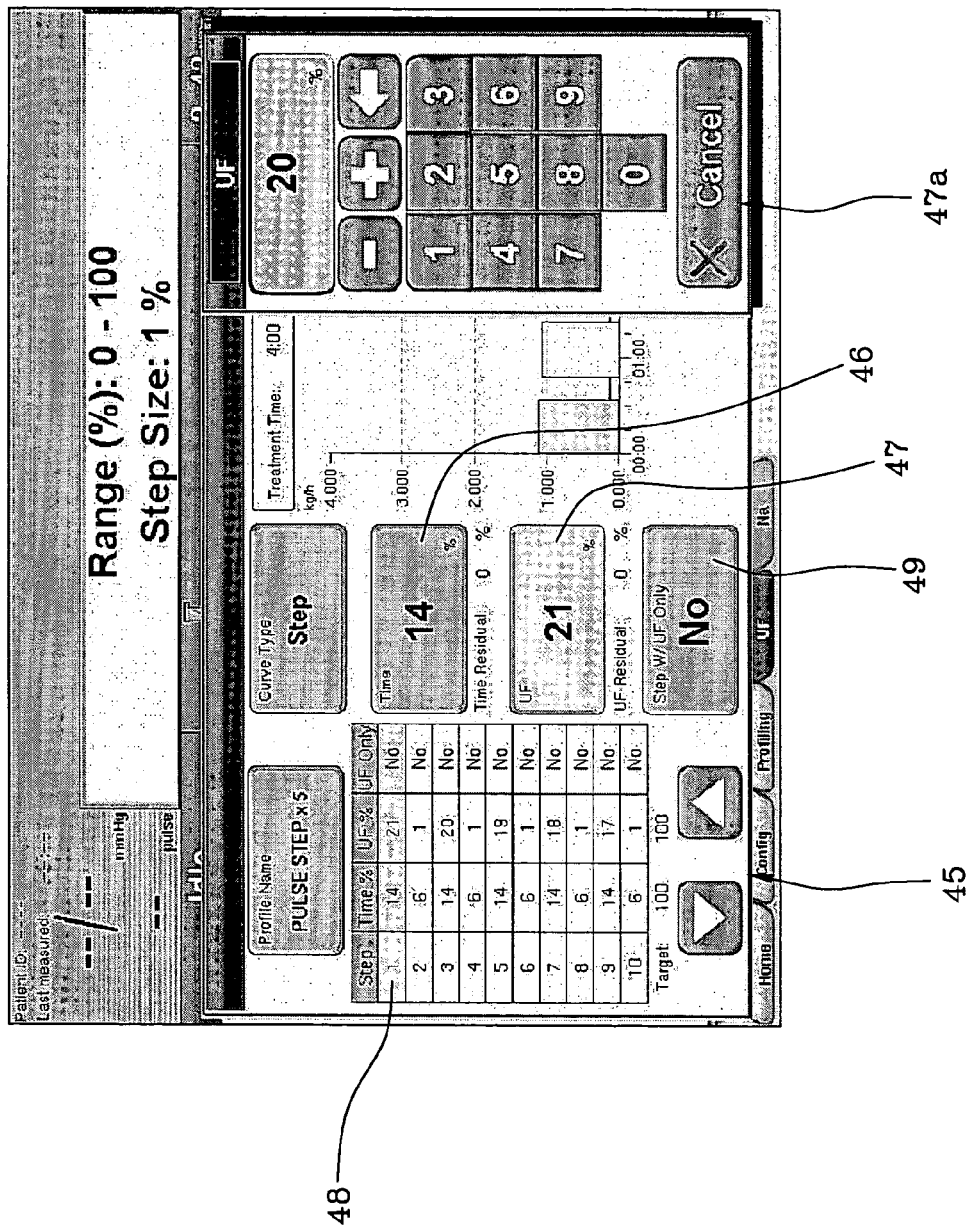
Figure 7:
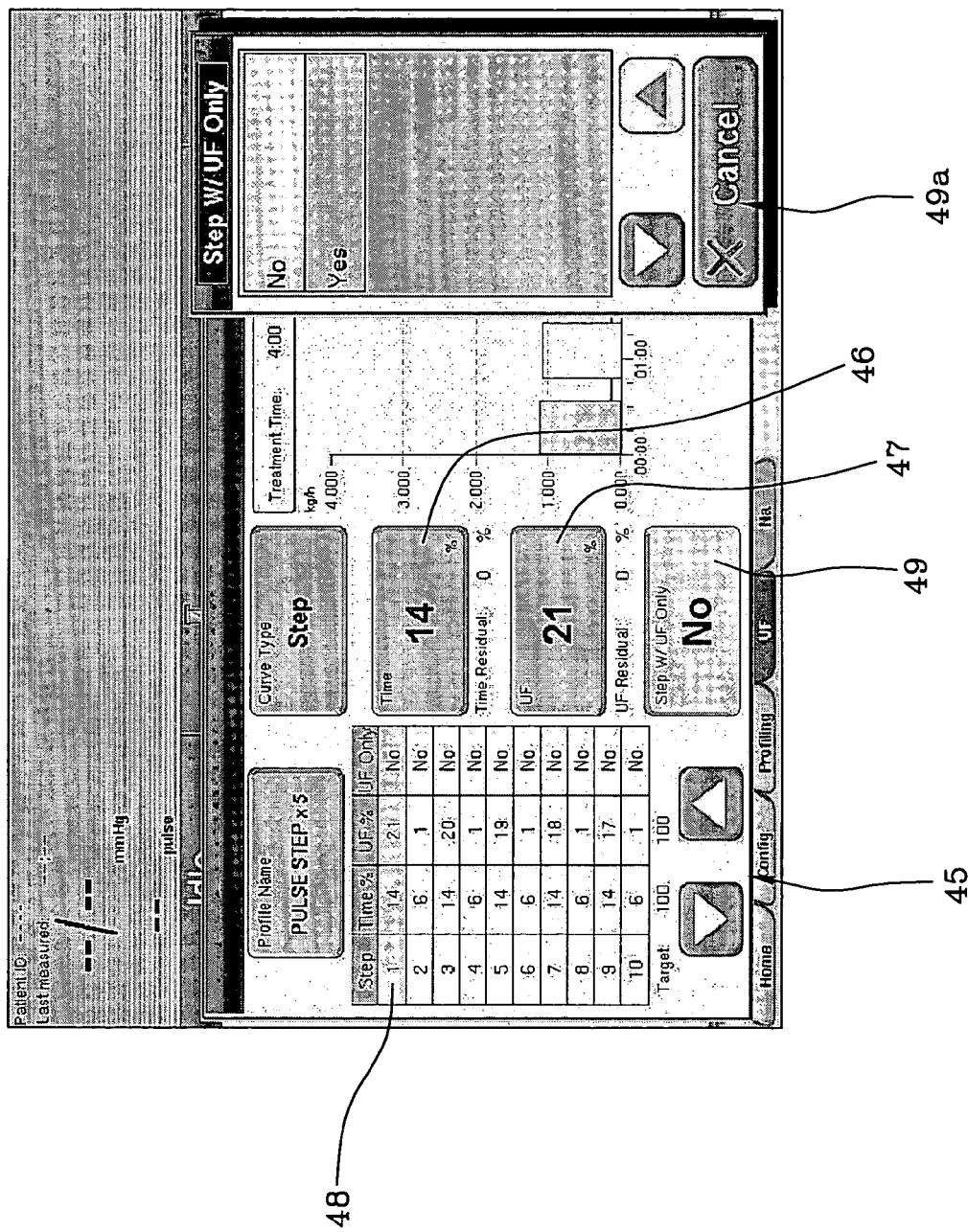

The control system is programmed for storing up to a pre-fixed maximum number of time interval values for each shaping profile: in the enclosed embodiment the control system allows to enter up to 10 time interval values corresponding to 10 time intervals which could have or not the same duration. This is for instance the case of FIG. 3. FIG. 4 shows the screen of FIG. 3 where a pop-up window 41 has been activated by the control system upon touch of the "edit selected profile" indicium 42 shown in FIG. 3. FIG. 4 shows in table form the ten steps of the shaping profile with the corresponding 10 time intervals values 40 (in percentages of total treatment time) and 10 reference values 39 (expressed in percentages of total weight loss).

In accordance with a further feature, the control system can also be programmed for associating to each pair a third value 43 indicating whether the respective pair refers or not to a pure ultrafiltration treatment step wherein the spent liquid flowing in the waste line 8 is corporeal fluid only coming from the second chamber 3 of the treatment unit 4 via filtration through the semipermeable membrane of the filter unit.

This being said in general terms, it should be noted that the control system could be programmed to store a plurality of shaping profiles.

In case the apparatus control system has one or more previously stored shaping profiles, then the user interface screen (see FIG. 3) displays a plurality of indicia 44 for allowing selection of the shaping profile: indeed the user can select and access a certain shaping profile for the purpose of simply visualizing it, or for modifying it or for creating a new profile. According to an embodiment of the invention upon selection of the shaping profile, the control system is programmed for displaying a graphic representation 45 of the selected shaping profile at least on a portion of said screen, the graphic representation can be a Cartesian representation (a two axis plot as in FIG. 3) wherein reference values are represented as percentages of the total weight loss and time intervals as percentages of the total treatment time and/or a multi column table representation (see FIG. 4), wherein again reference values are represented as percentages of the total weight loss and time intervals as percentages of the total treatment time. Practically since each respective reference value applies for the corresponding time interval, the resulting Cartesian representation is a histogram or bar graph wherein the height of each bar represents one of the values of each pair and wherein the thickness of each bar represents the other of the values in each pair. In FIG. 3 the eight of each bar represents the percentage of weight loss and the thickness of each bar the percentage of treatment time during which said weight loss should be achieved.

During configuration, in order to select and then modify the shaping profile, the control system displays the mentioned editing indicium 42 on a portion of said screen: selection of the editing indicium moves the user into a new screen or screen area (in FIG. 4 the mentioned pop-up window 41) where the shaping profile reference values and corresponding time interval values of the selected profile are displayed and can be modified for creating a new shaping profile.

The operator can act on suitable means of the user interface to modify one or more steps of the shaping profile. The control system of the enclosed embodiment is programmed for storing the new shaping profile if the sum of the reference values thereof and the sum of the time interval values do not exceed respective threshold values. For instance iii case of values stored as percentages, the control system allows storage of a new profile or of a modified profile only if the sum of the values makes 100%.

In greater detail, the modification step comprises the following sub steps: displaying a graphic representation of said shaping profile (for instance in table form as in FIG. 4 or in Cartesian form), displaying at least a first indicium 45 allowing to select one of said plurality of pairs of the shaping profile, displaying a second indicium 46 allowing to modify the time interval value of the selected pair. displaying a third indicium 47 allowing to modify the reference value of the selected pair. In practice, the first indicium 45 can be a touch sensitive area comprising arrow keys 45a, 45b, which, when selected, move a corresponding identifier 48 (which can be anything suitable for graphically or audibly identify a selection—in FIG. 4 the identifier is a background marking of the table line where the concerned pairs are represented) in correspondence of the selected step or pair to visually inform the user as to which values are under modification. Alternative means for identifying the pair under modification could also be envisaged, such as: directly touching the part of the screen where the pair is visually represented, or providing touch sensitive areas in correspondence of each representation of the pairs, etcetera. The second indicium 46 and the third indicium 47 can be touch sensitive areas, such as buttons on the touch screen which, when selected, call on screen a respective data entry display 46a, 46b (such as a pad) for entering a specific value.

When, as in the embodiment of enclosed drawings, each pair has a third value associated therewith also a fourth indicium 49 can be present for switching said third value between two conditions representing whether or not the respective pair is associated to a pure ultrafiltration step. The fourth indicium can be an on/off switch or a touch sensitive area such as a button on the touch screen which, when selected, calls on screen a respective data entry display 49a (such as a pad—see the embodiment of figure) for allowing the user to specify "yes" (when UF only step is programmed) or "no" (if a non UF only step is programmed).

Here below the working of the medical apparatus is described in detail referring to selection and 'then modification of ultrafiltration profiles during configuration and' referring to the embodiment of FIGS. 3 to 7. The left column indicates the operator's actions and the right column the apparatus reaction.

| Steps | |
|---|---|
| Operator Action | Apparatus reaction |
| 1. The user selects profile that is to be modified acting on a key 44. | |
| | 2. The machine displays the profile 38 in graphical formal |
| 3. The user selects button "edit selected profile" key 42. | |
| | 4. the machine displays the table of percentages: |
| | % Tie % Target Loss  UF Only (Y/N) |
| | % Time % TargetLoss  UF Only (Y/N) |
| | % Time % TargetLoss  UF Only (Y/N) |
| | % time % TargetLoss  UF Only (Y/N) |
| | . . .                . . . |
| | % Time % TargetLoss  UF Only (Y/N) |
| | Initially only the first row is displayed; the other rows in the table are made available depending on the first value inserted. The same concept is applied for the remaining rows. |
| 5. The user selects the pair he intends to modify acting on keys 45. | |
| | 6. The machine displays the relevant modifiable values for the profile: |
| | Time %, UF %, UF ONLY Status. |
| 7. The user selects one of the values acting on keys 46, 46, 349 | |
| | 8. The machine displays corresponding keypads 46a, 47a, 49a allowing the user to enter the new value for Time or UF or UF ONLY status. |
| 9. Whenever the user selects the Confirm hard-key: | |
| | 10. The machine shall store the library profile if all percentages are equal to 100%. |
| 11. Whenever the user selects the name of a profile: | |
| | 12. The machine shall display an alphanumeric keypad, which allows the user to enter a new parameter name for the profile. |

As a final remark note that the control system could also be programmed so that, in configuration mode, a graphic representation 50 of the time varying parameter (in this case weight loss rate) is generated by the selected shaping profile 38 applying defaults values for total treatment time and total weight loss. This is made to give the operator programming a new shaping profile immediate feedback as to a corresponding behavior of the net weight loss rate with average values of total weight loss and total treatment time.

Profiles Management During Apparatus Setup and During Operation of the Apparatus In the present description as apparatus setup we intend the moment wherein the machine is submitted to the preparation steps immediately before running a treatment. Setup is normally executed by nurses or by the patient himself and precedes the starting of the treatment. During setup, parameter values, including profiles if any, are set and will be then implemented by the apparatus control system at treatment start. After treatment start, the apparatus is in operation mode: in case of a dialysis apparatus as the one of the exemplifying embodiment of present description operation mode is also referred to as 'dialysis mode'. In operation (or dialysis) mode the apparatus delivers the prescribed treatment and the control system control one or more actuators in order to fulfill the settings of a number of parameters.

During setup the user interface enables setting of at least one time-varying parameter pertinent to operation of the apparatus or pertinent to a process to be performed by said apparatus. As mentioned the time varying parameter is defined by a plurality of different parameter values that the parameter shall take during operation of the apparatus. The user can therefore set the time-varying parameter and program, the machine to follow the parameter in the course of a determined time span.

In order to allow set up of the time-varying parameter, the control system is programmed for storing a plurality of shaping profiles, which form a shaping profiles library; the control system is programmed for allowing the user to select from the library of anyone of said shaping profiles. The control system then calculates the parameter values of the time-varying parameter starting from reference values of the selected shaping profile.

More in detail, for each shaping profile, the control system stores a, plurality of reference values defining the shaping profile, receives the value of at least a discriminating factor which relates to the time-varying parameter, and calculates each of the parameter values as a function of a corresponding reference value of the shaping profile and of the value of said discriminating factor.

The discriminating factor is a value that can be entered by the user (alternatively the control system could receive the value of the discriminating factor from other sources such as a patient card or a remote unit) and can represent one of the following values, which characterize the time-varying parameter:

an integral of the values that the time-varying parameter shall take over the treatment time;

a starting value that, shall be taken by the time-varying parameter at the beginning of the treatment time;

an intermediate value that shall be taken by the time varying parameter during the treatment time;

an end value that shall be taken by the time-varying parameter at the end of the treatment time;

a maximum value that shall not be passed by the time-varying parameter during the treatment time;

a minimum value that shall not be passed by the time-varying parameter during the treatment time;

an average over the treatment time of the values that the time-varying parameter shall take during the same treatment time.

According to one embodiment the reference values of the shaping profiles are expressed as percentages of the discriminating factor value and calculation of each parameter value comprises the step of multiplying each reference value by the value of said discriminating factor. According to one embodiment, the shaping profile is stored as a plurality of pairs, each, pair including a shaping profile reference value and a time interval value.

Each time interval value is either a fraction (for instance expressed as a percentage of total treatment time) of the total treatment time or a prefixed time interval.

The control system is programmed to receive said discriminating factor value and a total treatment time value (or several prefixed time interval values), and to calculate a profile for said time-varying parameter as function of the values of said plurality of pairs, of said discriminating factor value and, if time fractions are used, of the treatment time. More in detail the calculation comprises determining each of said plurality of parameter values by multiplying each reference value by the value of the discriminating factor divided by the time interval value, or the value of the discriminating factor, or a value proportional to the value of the discriminating factor. Then each parameter value is associated with the respective actual time interval during which the parameter value remains constant for forming a step shaped profile of said time-varying parameter.

According to one aspect of the invention the control system can be programmed to check the sum of the reference values and to generate an error signal if the sum is higher than a reference threshold value, and/or to check the sum of the time interval values and to generate an error signal if the sum is higher than a reference threshold value.

In the embodiment of the attached drawings the invention is applied to an extracorporeal blood treatment machine, in this case the time-varying parameter can be any parameter that the User may want to set at values varying in the course of the dialysis treatment session. For instance, by way of non-limiting example, a time varying parameter could be one of the following:

Temperature of the dialysis liquid,
Conductivity of the dialysis liquid,
Electrolytes concentration of the dialysis liquid,
Temperature of the substitution solution,
Conductivity of the substitution solution,
Electrolytes concentration of the substitution solution,
Flow rate of the dialysis liquid,
Flow rate of the spent liquid,
Flow rate of the substitution solution,
Flow rate of the blood in the in one of said tubing,
Ultrafiltration rate through the semipermeable membrane,
Net weight loss rate,
Net weight loss during a time interval,
Temperature of the of a medicament infusion solution,
Medicament concentration of a medicament infusion solution,
Flow rate of a medicament infusion solution.

In the embodiment shown in the attached figures, the time-varying parameter is the net weight loss rate (which in pure hemodialysis with no infusion corresponds to the ultrafiltration rate) and the discriminating factor value is the total weight loss to be achieved at the end of the total treatment time. The control system is then programmed to receive the value of the total weight loss as discriminating factor and a total treatment time, and to calculate a profile for said time-varying parameter as function of said plurality of reference value of the shaping profile, of said discriminating factor value and of the treatment time. In practice, the shaping profile cart be stored as a plurality of pairs where each pair includes a shaping profile reference value and a time interval value representing the time span during which the reference value applies. The reference values are represented as fraction of the total weight loss, while each time interval value is represented either as fraction of the total treatment time or as a prefixed actual time interval.

According to one embodiment the shaping profile reference values can be stored as percentages of the total weight loss and the time interval values of the shaping profile as percentages of the total treatment time. In this case the time varying profile would be calculated starting from the shaping profiles pairs and multiplying each reference value of the pair times the total weight loss value and multiplying each time interval value times the total treatment time thereby obtaining a plurality of pair defining the time varying profile.

Figure 8:
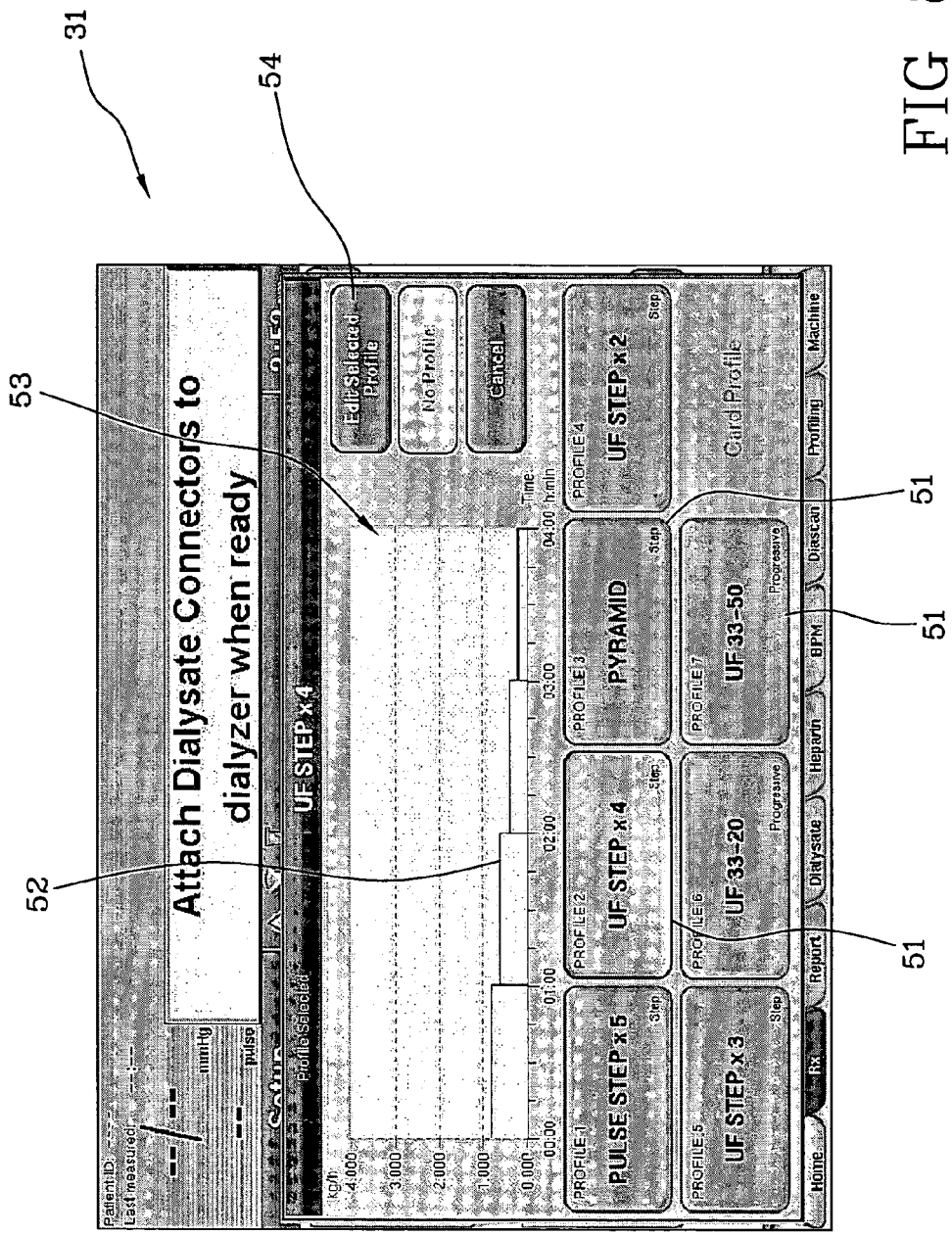
FIGS. 8 and 9 show a user interface according to the invention during the medical apparatus setup.

For instance, the control system can be programmed for, storing a plurality of shaping profiles to form a shaping profiles library; referring to FIG. 8 embodiment where the blood treatment apparatus user interlace has a touch screen, each shaping profile can be selected by a corresponding touch sensitive indicium 51, which is basically analogous to indicia 44 but for the fact that the machine is in setup mode. In practice, the control system allows selection of the total weight loss and of the total treatment time by means a data entry unit. The operator would then be allowed to select from the library any one of the shaping profiles. After selection of total treatment time, total weight loss, and shaping profile, the control system determines the plurality of pairs representing the profile of the time-varying parameter (each pair including a weight loss rate value and the corresponding actual time interval value during which the weight loss rate is constant) multiplying the time interval values by the total treatment time value to obtain actual time intervals and multiplying the shaping profile reference values by the value of the total weight loss divided by the respective actual time interval. Once the pairs are calculated, the control system can display the time-varying weight loss rate profile 52 on an area 53 of the screen.

A simple non-limiting example can be the following: the discriminating value can for instance be equal to 10 kg (overall weight loss), the total treatment time can be set at 3 hours and the selected shaping profile could be characterized by 3 the, reference values having the following values 10%, 40%, 50% (expressed as percentages of the total weight loss) and 3 corresponding time intervals of 1 hour each (which could alternatively be expressed in percentage term as 33%, 33%, and 33%).

Each value of the time varying profile (weight loss rate profile) would be calculated multiplying each percentage value times the value of the discriminating value thus obtaining 1 kg, 4 kg, and 5 kg and then dividing each of these values by the respective time interval of relevance. The time varying profile would then be characterized by a first step of 1 kh/hour for the first hour, by a second step of 4 kg/hour for the second hour and by a third step of 5 kg/hour for the third hours. Alternatively, in case the machine is programmed to work with prefixed time intervals, the control system can be programmed for allowing selection from the library of any one of the stored shaping profiles and allowing selection of the total weight loss. Then each pair of the time varying parameter actual profile (defined as a weight loss rate value and corresponding prefixed actual time interval value during which the weight loss rate is constant) would be calculated by multiplying the shaping profile reference values by the value of the total weight loss and dividing by the respective prefixed actual time interval.

Notice that according to this embodiment, the machine control system is programmed so that during setup mode of the machine the operator has to first select or render available to the control system the total weight loss and the total treatment time before being allowed to access selection of the desired shaping profile. In case a touch screen is used, then selection of a profile is made touching the respective indicium selection area. Therefore in case the total weight loss and/or the total treatment time are not available to the control system said touch sensitive indicia are either switched to a condition where they are disabled and not touch sensitive or they are simply not displayed at all.

According to a further alternative particularly suitable to intensive care treatments wherein the treatment time is often unknown and the average weight loss rate (or the weight loss to be reached a cross reference time interval) is the main parameter entered by the user, the reference profiles values could be stored as percentages of said average weight loss rate and the time intervals stored as prefixed values. In this case, the machine calculates the profile by multiplying each reference value time by the weight loss rate (this giving a profile of weight loss rates applicable during a prefixed treatment time). While running the treatment, the control system cyclically and continuously applies the profile as many times as necessary.

In setup mode the control system allows the user to modify the actual profile of the time-varying parameter. The modification of the profile is similar to the modification of the shaping profiles in configuration mode: notice however that modification of the actual profile in setup mode differs from modification of the shaping profiles during machine configuration, in that the profiles here are not described in terms of percentages, but in terms of their actual values calculated using the entered weight loss and treatment time total values.

Figure 9:
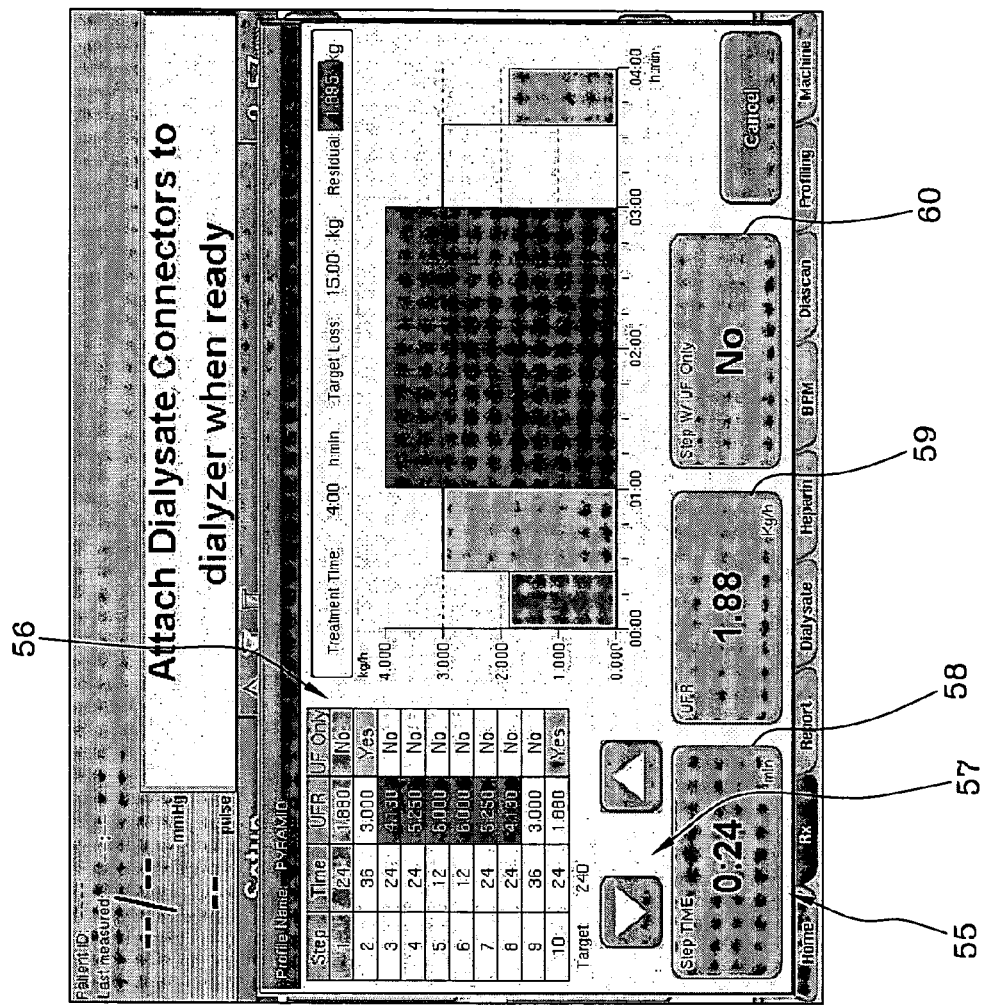

In order to access modification the user should press the "edit selected profile indicium" 54 of FIG. 8 and then access the 'screen or window 55 of FIG. 9 Which is very similar to window 41. Once the profile' values have been modified, the control system allows storing the new shaping profile if the sum of the reference values thereof and the sum of the time interval values do not exceed the total treatment time and the total weight loss. The embodiment of FIGS. 8 and 9, the modification of the profile comprises displaying a graphic representation 56 of said profile (in table and/or in plot form) and displaying the following indicia (which in case of a touch screen are, touch sensitive areas or buttons): a first indicium 57 allowing to select one of said plurality of pairs of the shaping profile, a second indicium 58 allowing to modify the time interval value of the selected pair, a third indicium 59 allowing to modify the reference value of the selected pair, and a fourth indicium 60 for switching said third value between two conditions representing whether or not the respective pair is associated to a pure ultrafiltration step. The selection of said indicia can call a respective pop-up window allowing the user to enter the new desired values as in configuration mode for the shaping profiles.

In case the user wants to create a brand new profile the control system could also be programmed for allowing entry of a plurality of reference values and corresponding time interval values of the new profile. Again the new profile can be stored in the profiles library only after verifying if the sum of the reference values and the sum of the time interval values do not exceed respective threshold values and transformed, before storage, into normalized values by dividing the absolute values of weight loss rate and time interval by total treatment time and total weight loss to generate a shaping profile.

Once the user has selected the profile for use during treatment (either by using pre-stored shaping profiles or by creating a new profile as above indicated), the user is can activate the dialysis treatment.

Alternatively the user could start the treatment with no profile selected, for instance with no weight loss rate profiling. In this case the apparatus runs the treatment at a constant weight loss rate, which can be either a default value or a value set by the operator. Even when the treatment starts at constant weight loss rate, still the control system can be programmed for allowing selecting a shaping profile after treatment start, computing the profile of the net weight loss rate using:

as total treatment time, the total treatment time entered at the beginning of the treatment less the elapsed treatment time and as total weight loss, the total weight loss entered at the beginning of the treatment less the fluid weight already removed.

On the other hand, in case the treatment starts with a certain shaping profile selected, and the operator wishes to modify total treatment time and/or total weight loss in the course of the treatment session, the control system can also be programmed for allowing modification of the total treatment time and/or total weight loss while treatment is in progress. In case total treatment time is changed the control system recalculates the weight loss rate profile data using the selected shaping profile and the new treatment time, taking into account the amount of time that has already passed since the treatment started. In case total weight loss is changed, the control system is programmed for recalculating the weight loss rate profile data using the selected shaping profile and the new weight loss, taking into account the amount of fluid that has already been removed since the treatment started.

Additionally in case an operator desires to deactivate during treatment a previously activated weight loss rate profile, the control system is programmed for setting the net weight loss rate to a constant value equal to the difference (target total weight loss—already removed fluid) divided by the time remaining in the treatment.

A further separate feature of the invention consists in that the control system is programmed for starting an error compensation procedure if the set total weight loss cannot be reached using the set weight loss rate profile; the compensation procedure is useful for instance when the machine has not achieved in reality the, weight loss the operator expected with the set profile (this could happen in case of malfunctioning for instance). The compensation procedure is also useful if the user modifies in the course of the treatment the desired weight loss and/or treatment time in a way that the set profile is unable to fulfill. The compensation procedure, which can be started by the operator or automatically started by the control system, comprises the following steps:

computing an weight loss deficit as an extra amount of fluid that should be removed to fulfill the set total weight loss, adding the weight loss deficit proportionally to the remaining steps in the step profile controls the weight loss rate according to the new profile In order to avoid that the calculated weight loss rate profile presents weight loss rate values which are not acceptable for a specific patient or user, the control system is programmed for comparing each value of the weight loss rate profile with an acceptable threshold checking if all steps of the of the weight loss rate profile are greater than or equal to the minimum allowed UF value and if all steps of the ultrafiltration profile are lower than a maximum allowed UF value.

The control system during setup, or during dialysis, or during compensation allows storing and execution of a profile only if above check is positively passed.

Figure 10:
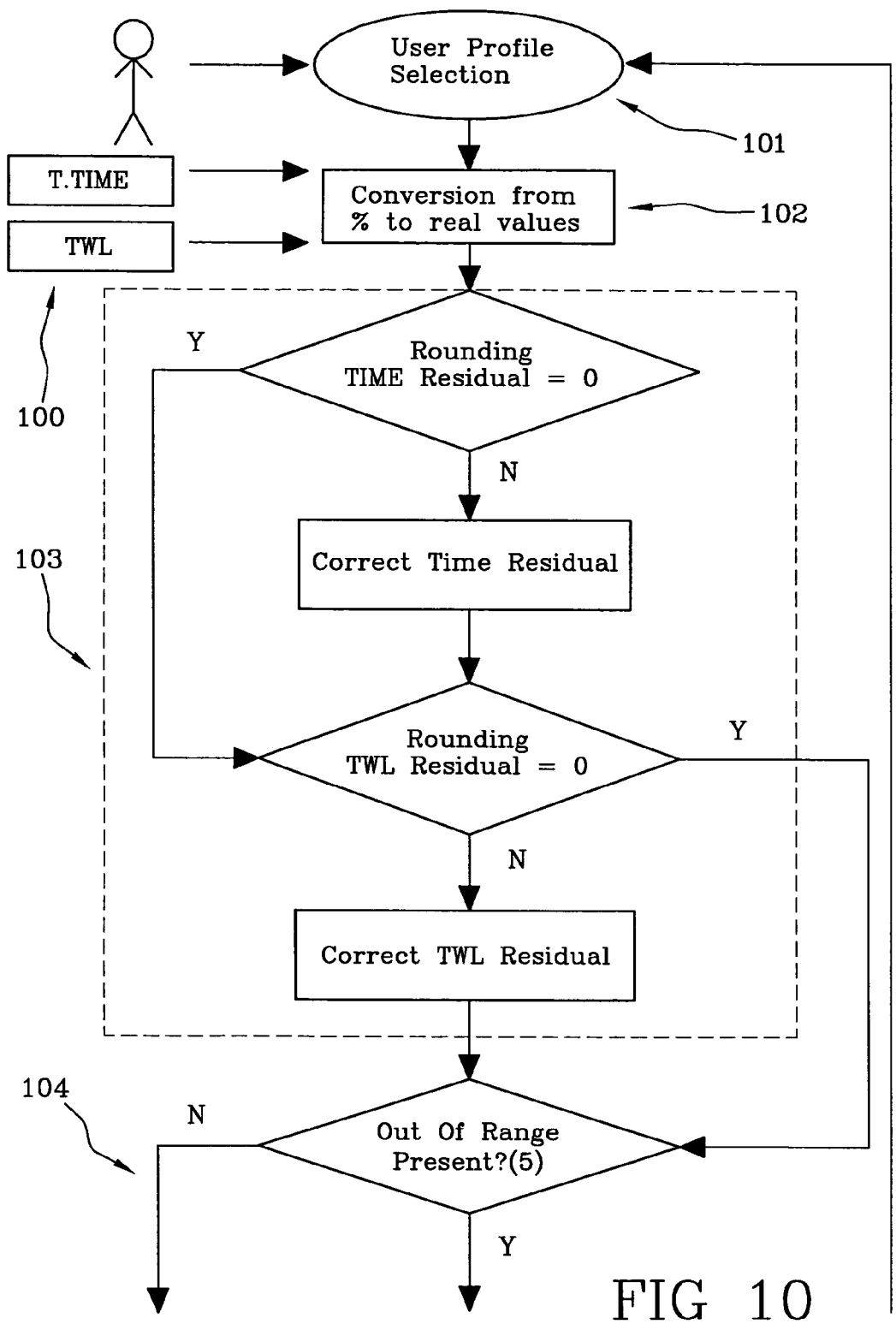
FIGS. 10 and 11 shows a flowchart of the working of an embodiment of a medical apparatus or user interlace of the present invention.
Figure 11:
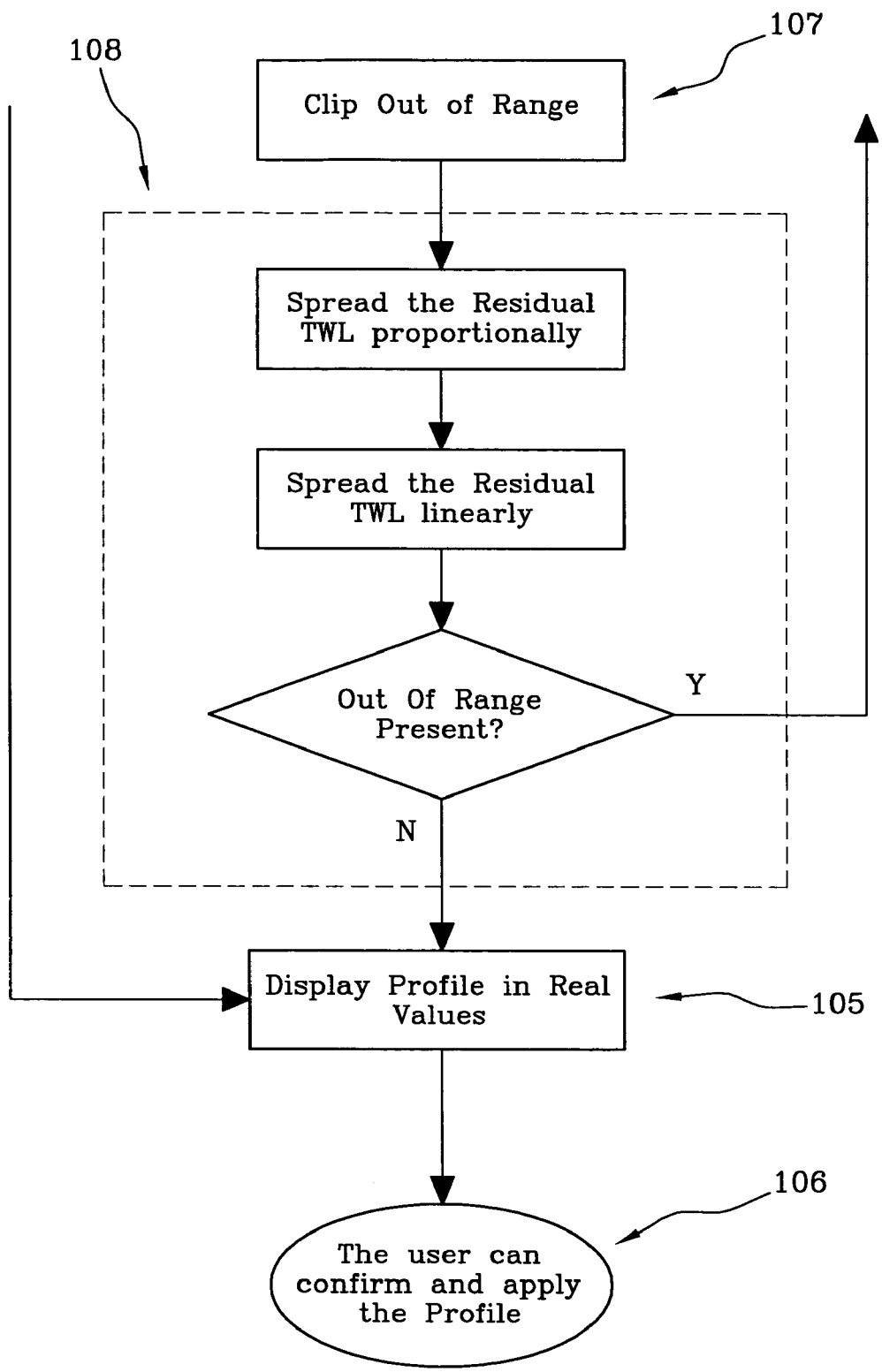

A possible embodiment and working of the present invention during set-up is described here below with the aid of the flowchart shown in FIGS. 10 and 11.

Figure 12:
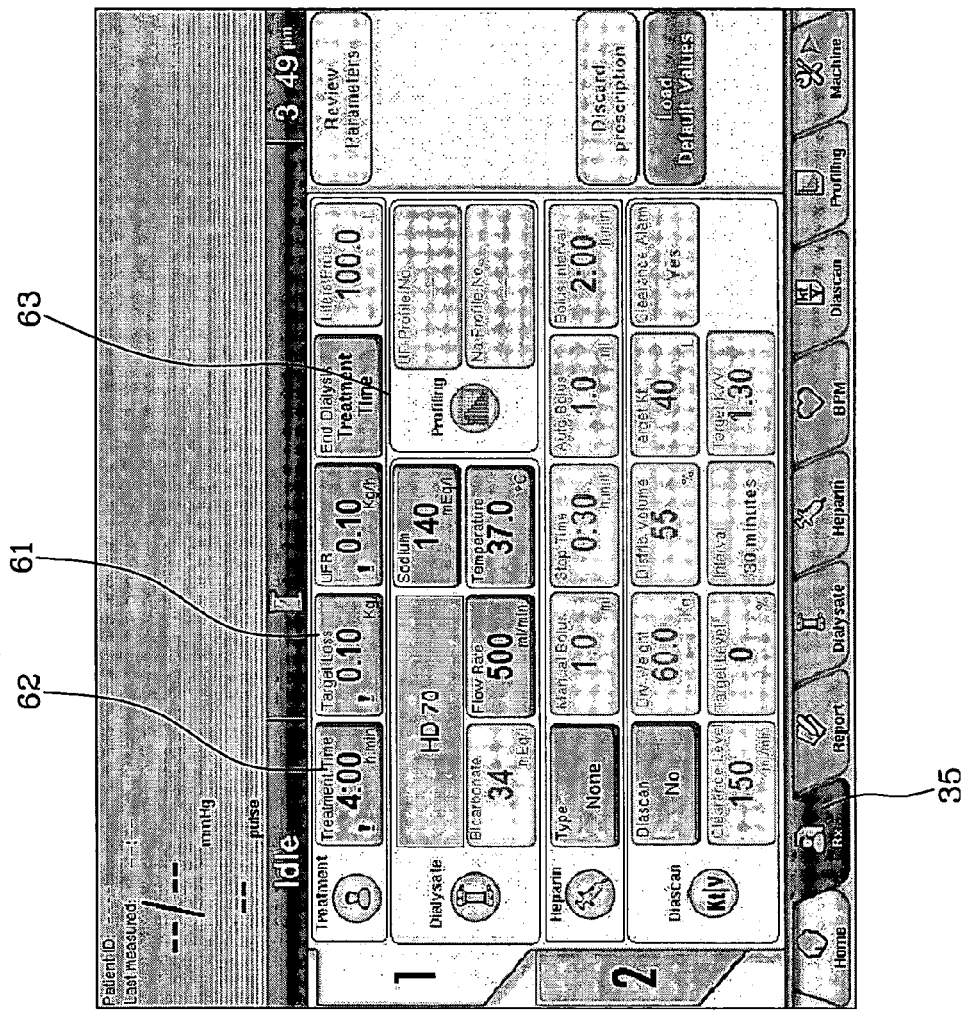

As a first step 100, the user inserts Dialysis Total treatment Time (T) and Total Weight Loss (TWL). At this purpose in the embodiment here described the user by operating on navigation keys 35 can access screen of FIG. 12 and enter TWL and T using touch buttons 81 and 62. In this embodiment the control system cannot create an actual weight loss rate profile without the selected shaping profile and the values of TWL and T. The user must insert T and TWL in order to make available the Choose Profile Button 63 which is showing two selectable types of parameters: sodium or UF (weight loss rate). The user presses button 63 and enters the screen of FIG. 8 where he has then to select the desired Profile (step 101 in the flowchart of FIGS. 10 and 11) and the control system can then calculate a real Profile, using the percentages of the shaping profile, T and TWL (step 102).

The conversion from percentage to real values, usually introduces little "errors" due to numerical rounding. A routine in the control system corrects for these little Time errors and TWL errors spreading linearly (i.e. dividing the error by the number of steps and equally adding/subtracting the divided error to each real value) the residuals (step 103).

As mentioned the weight loss rate (UFR) represented by the actual weight loss rate profile must, at each time step, be greater equal than a minimum (MinUFR) and less-equal than a maximum (MaxUFR). The control system therefore starts a routine (step 104 in FIG. 10) that checks if there are points on the profile out of the range [MinUFR, MaxUFR]. If all the profile is inside this interval, the control system displays it and the user can confirm it (steps 105 an 106 in FIG. 11). If the routine finds points out of range, it clips the points (step 107 in FIG. 11): this means that a value less then MinUFR is set to MinUFR and a value greater than MaxUFR is set to MaxUFR (refer for instance to FIG. 9 where weight loss rates higher than 4 kg/h are set at 4 kg/h).

If in the step 104 the control system finds any out of range to clip, the profile resulting out of step 107 would not match the TWL. Therefore the control system starts a routine that tries to recover the TWL spreading the quantity ReSTWL= (TWL—integral of the curve resulting from step 107): this means the control system routine tries to add to the clipped Profile the lacking TWL (step 108). This is performed in three steps:

Spread the ResTWL proportionally (i.e. a proportionally to the real value of each step) preventing out of range, if now ResTWL=0, the Profile is valid, else Spread the remaining ResTWL linearly (i.e. equally) along the Profile preventing out of range; if now ResTWL=0, the Profile is valid, else There is no chance to spread the ResTWL preventing out of range and the control system starts then a routine that "looks" again for out of range points. If all the Profile is in the valid range, then the profile can be confirmed; else the confirmation is prevented and the user must change T and/or TWL.

Here below the working of a medical apparatus according to a further embodiment of the invention is described referring to selection and then modification of weight loss rates profiles during setup and during subsequent starting of apparatus operation for delivering a dialysis treatment. The left column indicates the operator's actions and the right column the apparatus reaction.

| Steps | |
| --- | --- |
| Operator Action | Apparatus reaction |
| 1. The operator inputs the TX time value. | |
| 2. The operator inputs the Target Loss value. | |
| | 3. If both Tx Time and Target Loss have been input, the machine control system makes a UF Profile parameter button available for use. |

-continued

| Operator Action | Apparatus reaction |
|---|---|
| 4. The operator selects the UF Profile parameter button. | |
| | 5. The apparatus control system allows the operator to choose one of the name library shaping profiles 51 (or none). |
| 6. The operator selects the profile. | |
| | 7. The apparatus shall: a. Compute the profile based on the Treatment Time, the values and/or percentages specified in the library profile, and the Target Loss (if it is a UF profile). b. Display a graphical representation 52 of the computed curve in terms of UFR and time, along with a CANCEL Action Key. |
| 8. IF the user selects the CONFIRM button: | |
| | 9. The apparatus shall store the UF profiling parameter for use in the treatment. |
| 10. ELSE IF the user selects the EDIT Action Key: | |
| | 11. The apparatus shall allow the user to edit the profile, and activate the "editing procedure during the setup here below separately described. |
| 12. ELSE IF the user selects the CANCEL Action Key: | |
| | 13. The apparatus shall close the popup. |
| 14. WHENEVER the user selects the DIALYSIS Action key to go into dialysis (i.e. starts a dialysis treatment where the actuators of apparatus 1 are controlled to generate a weight loss rate following the set profile): | |
| | 15. The apparatus shall start controlling the UF according to the profile selected, if any. |
| 16. WHENEVER the user chooses a profile after the DIALYSIS Action key is entered. | |
| | 17. The apparatus will compute the profile from the indicated profile library as above. The Tx Time used will be the original Tx Time minus the time that has already elapsed since the treatment start. Likewise, the Target Loss used in the calculation will be the original Target Loss minus the fluid already removed. |
| 18. WHENEVER the user modifies the Tx Time (total treatment time) or Target Loss (total weight loss) while at treatment is in progress: | |
| | 19. For all profiles that are affected by the change, the apparatus shall: a. Recalculate the profile data using the original library profile and the new treatment time, but taking into account the amount of time that has already progressed. that is, the profile computations continue from the time the recalculation is performed (the profile does not start over from the beginning). b. Display the new profile to the user in a popup for confirmation. |
| 20. When the user CONFIRMS the new profile: | |
| | 21. The apparatus shall erase the confirmation popup. Not it is assumed here that if the new profile is not desired, the user will change the Tx Time or Target Loss to a more appropriate value. |
| 22. WHENEVER the operator deactivates a UF profile during a treatment, by pushing the DEACTIVATE UF Action Key under the Profile Screen: | |
| | 23. The apparatus displays a keypad for changing the UFR, with the default UF Rate set to the target loss remaining divided by the time remaining in the treatment. The operator must confirm this value or choose a new UFR value. 24. WHENEVER an alarm or a situation occurs indicating that the requested Target Loss cannot be achieved (due to the apparatus being in Minimum UF for an extended amount of time), the apparatus shall make the COMPENSATE Action Key available. |
| 25. WHEN the user presses the COMPENSATE Action Key: | |
| | 26. The apparatus shall: a. Compute the UF deficit (amount that should have been removed minus the amount that has actually been removed) b. Add the UF deficit proportionally to the remaining steps in the step profile. c. Compute the new profile and display a popup with the profile shown graphically. d. Display an operator message in the Operator's Message box such as "Confirm or Cancel the new profile" |
| 27. IF the user Confirms the new profile: | |
| | 28. The apparatus controls the UFR according to the new profile |
| 29. IF the user Cancels the new profile: | |
| | 30. The apparatus controls the UF R according to the previous profile. |

Here below the working of the medical apparatus is described referring to the editing procedure for modification of a selected profile during setup or during apparatus operation (dialysis mode). The left column indicates the operators actions and the right column the apparatus reaction.

| Steps | |
| --- | --- |
| Operator Action | Apparatus reaction |
| 1. The user selects the EDIT SELECTED PROFILE Key for a profile, either as part of a confirmation popup or under an appropriate navigation tab: | |
| | The control system displays the profile in graphical format. UFR- Time UFR UF Only (Y/N) Time UFR UF Only (Y/N) Time UFR UF Only (Y/N) ... Time UFR UF Only (Y/N) |
| 2. When the user selects an entry none of the tables: | |
| | 3. The apparatus shall display a keypad allowing the user to enter the new value for that entry. |
| 4. When the user selects the Confirm hard key: | |
| | 5. The apparatus stores the profile table or parameters into memory for later use. |

Software Program Product

The invention also concerns a software program comprising instructions which, when executed by the main control system of the apparatus 1 or of the user interface, programs the control system to execute the control system steps which have been already disclosed in the chapter 'user Interface' and therefore not herein repeated.

The software program can be stored in any adequate support and then sold separately from the medical apparatus 1. In practice the software program could be stored on a magnetic recording support (for instance an hard disk, a cassette, a floppy disk, etcetera), or on an optical recording support (DVD or CD or other), on an electrical or electromagnetic carrier signal (if for instance the program is sent via a network), or on a computer readable memory (ROM, EPROM, RAM), or other convenient support memory device and then associated to the apparatus control system which running the program stored on said support is then programmed to render available a user interface having the features above described.

The invention claimed is:

1. A blood treatment apparatus comprising:
at least a user interface for enabling setting of at least one time-varying parameter pertinent to operation of said apparatus or pertinent to a process to be performed by said apparatus, the time-varying parameter being defined by a plurality of different parameter values that the at least one time-varying parameter takes during operation of the apparatus; and
a control system programmed to control operation of said blood treatment apparatus, the control system being connected to the user interface and being responsive to actions by a user on said user interface, said control system being programmed to:
store a plurality of reference values defining a shaping profile,
store the value of at least a discriminating factor which relates to the time-varying parameter, and
calculate each of the parameter values as a function of a corresponding reference value of the shaping profile and of the value of said discriminating factor, wherein each of said reference values is represented as a fraction of the discriminating factor value, and wherein the calculation of each parameter value comprises the step of multiplying each reference value by the value of said discriminating factor.

2. A blood treatment apparatus according to claim 1, wherein the control system is further programmed to:
store a plurality of shaping profiles to form a shaping profiles library, allowing selection from the shaping profiles library of any of said shaping profiles, and to calculate the parameter values starting from reference values of the selected shaping profile.

3. A blood treatment apparatus according to claim 1, wherein said discriminating factor is one selected from the group comprising:
an integral of the values that the time-varying parameter takes over a treatment time;
a starting value taken by the time-varying parameter at the beginning of a treatment time;
an intermediate value taken by the time-varying parameter during a treatment time;
an end value taken by the time-varying parameter at the end of a treatment time;
a maximum value that is not exceeded by the time-varying parameter during a treatment time;
a minimum value below which the time-varying parameter will not drop during a treatment time; and
an average over a treatment time of the values that the time-varying parameter will take during the treatment time.

4. A blood treatment apparatus according to claim 3, wherein the control system is programmed to allow the user to set said discriminating factor value.

5. A blood treatment apparatus according to claim 1, wherein said shaping profile is stored as a plurality of pairs, each pair including a shaping profile reference value and a time interval value.

6. A blood treatment apparatus according to claim 5, wherein each time interval value is one of:
a fraction of the total treatment time, and
a prefixed time interval.

7. A blood treatment apparatus according to claim 6, wherein the control system is programmed to receive said value of said discriminating factor and a total treatment time, and to calculate a profile for said time-varying parameter,
wherein the profile for said time-varying parameter is calculated by determining each of said plurality of parameter values by:
multiplying each reference value by one of a value of the discriminating factor divided by the time interval value, a value of the discriminating factor, and a value proportional to a value of the discriminating factor; and
associating to each parameter value the actual time interval during which the parameter value remains constant for forming a step-shaped profile of said time-varying parameter.

8. A blood treatment apparatus according to claim 6, wherein the control system is programmed to check a sum of the time interval values and to generate an error signal if the sum is higher than a reference threshold value.

9. A blood treatment apparatus according to claim 1, wherein the control system is programmed to check a sum of the reference values and to generate an error signal if the sum is higher than a reference threshold value.

10. A blood treatment apparatus according to claim 1, wherein the blood treatment apparatus is an extracorporeal blood treatment machine comprising:

a treatment liquid line for providing fresh dialysis liquid, fresh substitution solution, or both fresh dialysis liquid and fresh substitution solution;

at least a waste line for receiving spent liquid; and a blood treatment unit having a first chamber connected to the treatment liquid line and to the waste line, and a second chamber connected to a blood removal line and to a blood return tubing, said first and second chambers being separated by a semipermeable membrane;

wherein the time-varying parameter is one of:
temperature of the dialysis liquid;
conductivity of the dialysis liquid;
electrolyte concentration of the dialysis liquid;
temperature of the substitution solution;
conductivity of the substitution solution;
electrolyte concentration of the substitution solution;
flow rate of the dialysis liquid;
flow rate of the spent liquid;
flow rate of the substitution solution;
flow rate of the blood in one of said tubing;
ultrafiltration rate through the semipermeable membrane;
net weight loss rate;
net weight loss during a time interval;
temperature of a medicament infusion solution;
medicament concentration of a medicament infusion solution; and
flow rate of a medicament infusion solution.

11. A blood treatment apparatus according to claim 10, wherein the time-varying parameter is the net weight loss rate, and wherein the control system is programmed for: allowing starting of the blood treatment allowing to select a shaping profile after treatment start, and computing the profile of the net weight loss rate using, as total treatment time, the total treatment time entered at the beginning of the treatment less the elapsed treatment time and using, as total weight loss, the total weight loss entered at the beginning of the treatment less the fluid weight already removed.

12. A blood treatment apparatus according to claim 10, wherein the time-varying parameter is the net weight loss rate and wherein the control system is programmed for: allowing starting of the blood treatment, allowing modification of the total treatment time while treatment is in progress, recalculating the weight loss rate profile data using the selected shaping profile and the new treatment time, taking into account the amount of time that has already elapsed since a start of the treatment.

13. A blood treatment apparatus according to claim 10, wherein the time-varying parameter is the net weight loss rate, and wherein the control system is programmed for: allowing starting of the blood treatment, allowing modification of the total weight loss while treatment is in progress, and recalculating the weight loss rate profile data using the selected shaping profile and the new weight loss, taking into account the amount of fluid that has already been removed since treatment start.

14. A blood treatment apparatus according to claim 10, wherein the time-varying parameter is the net weight loss rate, and wherein the control system is programmed for: allowing starting of a blood treatment session and allowing deactivation of a previously activated weight loss rate profile during a treatment, the control system setting the net weight loss rate to a constant value equal to a target total weight loss remaining divided by a time remaining in the treatment.

15. A blood treatment apparatus according to claim 10, wherein the time-varying parameter is the net weight loss rate, and the control system is programmed for starting an error compensation procedure if a set total weight loss cannot be reached using a set weight loss rate profile, the compensation procedure comprising the following steps:
computing an UF deficit as an extra amount of fluid that should be removed to fulfill the set total weight loss, and
adding the UF deficit proportionally to the remaining steps in the step profile controls the UF rate to according to the new profile.

16. A blood treatment apparatus according to claim 10, wherein the time-varying parameter is the net weight loss rate, and wherein the control system is programmed for comparing each value of an ultrafiltration profile with an acceptable threshold.

17. A blood treatment apparatus according to claim 10, wherein the time-varying parameter is the net weight loss rate, and wherein the control system is programmed for:
checking if all steps of an ultrafiltration profile are greater than or equal to the minimum allowed UF value and if all steps of the ultrafiltration profile are lower than a maximum allowed UF value, and for allowing storing and execution of a profile only if above check is positively passed.

18. A blood treatment apparatus according to claim 1, wherein the time-varying parameter is one of:
net weight loss rate, and
net weight loss during a time interval.

19. A blood treatment apparatus according to claim 18, wherein the control system is programmed to receive said value of said discriminating factor and a total treatment time, and to calculate a profile for said time-varying parameter as function of said plurality of reference values of the shaping profile, of said discriminating factor value and of the treatment time.

20. A blood treatment apparatus according to claim 19, wherein said discriminating factor value is the total weight loss to be achieved at the end of said total treatment time.

21. A blood treatment apparatus according to claim 20, wherein:
said shaping profile is stored as a plurality of pairs, each pair including a shaping profile reference value and a time interval value,
each reference value is represented as fraction of the total weight loss, and
each time interval value is represented either as fraction of the total treatment time or as a prefixed actual time interval.

22. A blood treatment apparatus according to claim 21, wherein the control system is programmed for associating to each pair a third value indicating whether the respective pair refers to a pure ultrafiltration treatment step wherein the spent liquid flowing in the waste line is corporeal fluid only, said corporeal fluid coming from the second chamber of the treatment unit via filtration through said membrane.

23. A blood treatment apparatus according to claim 20, wherein the control system is programmed for:
storing a plurality of shaping profiles to form a shaping profiles library,
allowing selection of the total weight loss and of the total treatment time
allowing selection from the shaping profiles library of any of said shaping profiles,
multiplying the shaping profile reference values by the value of the total weight loss for obtaining a plurality of actual weight loss portions,
multiplying the time interval values by the total treatment time value to obtain actual time intervals, and associating each actual weight loss portion with the respective actual time interval during which the actual weight loss portion will be achieved.

24. A blood treatment apparatus according to claim 20, wherein the control system is programmed for:
   storing a plurality of shaping profiles to form a shaping profiles library,
   allowing selection of the total weight loss and of the total treatment time,
   allowing selection from the shaping profiles library of any of said shaping profiles, multiplying the time interval values by the total treatment time value to obtain actual time intervals, and
   multiplying the shaping profile reference values by the value of the total weight loss and dividing by the respective actual time interval for obtaining a plurality of pairs representing the profile of said time-varying parameter, each pair including a weight loss rate value and the corresponding actual time interval value during which the weight loss rate is constant.

25. A blood treatment apparatus according to claim 20, wherein the control system is programmed for:
   storing a plurality of shaping profiles to form a shaping profiles library,
   allowing selection from the shaping profiles library of any of said shaping profiles,
   allowing selection of the total weight loss, and
   multiplying the shaping profile reference values by the value of the total weight loss and dividing by the respective prefixed actual time interval for obtaining a plurality of pairs representing the profile of said time-varying parameter, each pair including a weight loss rate value and the corresponding prefixed actual time interval value during which the weight loss rate is constant.

26. A blood treatment apparatus according to claim 1 wherein the shaping profile is stored as a plurality of pairs, each pair including a shaping profile reference value and a respective time interval value,
   wherein each time interval is one of:
      a fraction of the total treatment time, and
      a prefixed time interval, and
   wherein each reference value being stored as a fraction of total weight loss to be removed by a patient during said total treatment time.

27. A blood treatment apparatus according to claim 26, wherein the control system is programmed for allowing storage of a plurality of shaping profiles.

28. A blood treatment apparatus according to claim 27, wherein the control system is programmed for storing up to a pre-fixed maximum number of time interval values for each shaping profile.

29. A blood treatment apparatus according to claim 26, wherein the control system is programmed for associating to each pair a third value indicating whether the respective pair refers or not to a pure ultrafiltration treatment step wherein the spent liquid flowing in the waste line is corporeal fluid only, said corporeal fluid coming from the second chamber of the treatment unit via filtration through said membrane.

30. A blood treatment apparatus according to claim 26, wherein the user interface includes at least a screen for displaying a plurality of indicia for allowing selection of the shaping profile.

31. A blood treatment apparatus according to claim 30, wherein, upon selection of the shaping profile, the control system is programmed for displaying a graphic representation of the selected shaping profile at least on a portion of said screen, said graphic representation being one of:
   a Cartesian representation wherein reference values are represented as percentages of the total weight loss and time intervals as percentages of the total treatment time, and
   a table representation, wherein reference values are represented as percentages of the total weight loss and time intervals as percentages of the total treatment time.

32. A blood treatment apparatus according to claim 30, wherein the control system is programmed for:
   allowing selection of a shaping profile;
   allowing modification of one or more of the reference values or time interval values of the selected shaping profile for creating a new shaping profile; and
   storing the new shaping profile if a sum of the reference values thereof and the sum of the time interval values do not exceed respective threshold values.

33. A blood treatment apparatus according to claim 32, wherein the modification step comprises:
   displaying an editing indicium on a portion of said screen,
   allowing selection of the editing indicium,
   upon selection of the editing indicium, displaying the shaping profile reference values and corresponding time interval values of the selected profile, and
   allowing change of one or more of the reference values or time interval values for creating a new shaping profile.

34. A blood treatment apparatus according to claim 32, wherein said modification step comprises the following sub steps:
   displaying a graphic representation of said shaping profile,
   displaying at least a first indicium allowing to select one of said plurality of pairs of the shaping profile,
   displaying a second indicium allowing to modify the time interval value of the selected pair, and
   displaying a third indicium allowing to modify the reference value of the selected pair.

35. A blood treatment apparatus according to claim 34, wherein the control system is programmed for associating to each pair a third value indicating whether the respective pair refers to a pure ultrafiltration treatment step where the spent liquid flowing in the waste line is corporeal fluid and wherein said modification step comprises the further step of displaying a fourth indicium for switching said third value between two conditions representing whether the respective pair is associated to a pure ultrafiltration step.

36. A blood treatment apparatus according to claim 30, wherein the control system is programmed for allowing creation of a new shaping profile, said creation comprising the following sub-steps:
   allowing entry of a plurality of reference values and corresponding time interval values,
   verifying if the sum of the reference values and the sum of the time interval values do not exceed respective threshold values, and
   storing the pairs of newly entered reference values and corresponding time interval values to form a new shaping profile if the verification step has been passed.

37. A blood treatment apparatus according to claim 30, wherein the control system is programmed to first allow entry of the total weight loss and of the total treatment time before allowing selection of one of said plurality of indicia.

38. A blood treatment apparatus according to claim 37, wherein the control system is programmed so that selection of a profile indicium causes displaying of a screen comprising a two axis plot wherein the calculated weight loss rate values and the corresponding actual time interval values during which the weight loss rate is constant are represented.

39. A blood treatment apparatus according to claim 30, wherein the control system is programmed so that selection of a profile indicium causes displaying of a screen comprising a two axis plot wherein the reference values and the corresponding time interval values are represented.

40. A blood treatment apparatus according to claim 30, wherein the screen comprises a touch screen, and the step of allowing selection of the indicium comprises detecting a touching of an indicium selection area.

41. A blood treatment apparatus comprising:
at least a user interface for enabling setting of at least one time-varying parameter pertinent to operation of said apparatus or pertinent to a process to be performed by said apparatus, the time-varying parameter being defined by a plurality of different parameter values that the at least one time-varying parameter will take during operation of the apparatus; and
a control system programmed to control operation of said blood treatment apparatus, the control system being connected to the user interface and being responsive to actions by a user on said user interface, said control system being programmed to:
store a plurality of reference values defining a shaping profile, wherein said shaping profile is stored as a plurality of pairs, each pair including a shaping profile reference value and a time interval value,
store the value of at least a discriminating factor which relates to the time-varying parameter, the time-varying parameter being the net weight loss rate, and the value of the discriminating factor being the total weight loss to be achieved at the end of a total treatment time, and
calculate each of the parameter values as a function of a corresponding reference value of the shaping profile and of the value of said discriminating factor by:
multiplying the time interval values by the total treatment time value to obtain actual time intervals, and
multiplying the shaping profile reference values by the value of the total weight loss and dividing by the respective actual time interval for obtaining a plurality of pairs representing the profile of said time-varying parameter, each pair including a weight loss rate value and the corresponding actual time interval value during which the weight loss rate is constant.

42. A blood treatment apparatus comprising:
at least a user interface for enabling setting of at least one time-varying parameter pertinent to operation of said apparatus or pertinent to a process to be performed by said apparatus, the time-varying parameter being defined by a plurality of different parameter values that the at least one time-varying parameter will take during operation of the apparatus; and
a control system programmed to control operation of said blood treatment apparatus, the control system being connected to the user interface and being responsive to actions by a user on said user interface, said control system being programmed to:
store a plurality of reference values defining a shaping profile,
store the value of at least a discriminating factor which relates to the time-varying parameter, the time-varying parameter being the net weight loss rate, and the value of the discriminating factor being the total weight loss to be achieved at the end of a total treatment time, and
calculate each of the parameter values as a function of a corresponding reference value of the shaping profile and of the value of said discriminating factor by:
multiplying the shaping profile reference values by the value of the total weight loss and dividing by a respective pre-fixed actual time interval for obtaining a plurality of pairs representing the profile of said time-varying parameter, each pair including a weight loss rate value and the corresponding pre-fixed actual time interval value during which the weight loss rate is constant.

43. A blood treatment according to claim 42, wherein the control system is further programmed to:
store a plurality of shaping profiles to form a shaping profiles library, allowing selection from the shaping profiles library of any of said shaping profiles, and to calculate the parameter values starting from reference values of the selected shaping profile.

44. A blood treatment according to claim 42, wherein the control system is programmed to allow the user to set said discriminating factor value.

45. A blood treatment apparatus according to claim 42, wherein the control system is programmed to check a sum of the reference values and to generate an error signal if the sum is higher than a reference threshold value.

46. A blood treatment apparatus according to claim 42, wherein the shaping profile includes a plurality of time interval value, and wherein the control system is programmed to check a sum of the time interval values and to generate an error signal if the sum is higher than a reference threshold value.

47. A blood treatment apparatus comprising:
at least a user interface for enabling setting of at least one time-varying parameter pertinent to operation of said apparatus or pertinent to a process to be performed by said apparatus, the time-varying parameter being defined by a plurality of different parameter values that the at least one time-varying parameter takes during operation of the apparatus; and
a control system programmed to control operation of said blood treatment apparatus, the control system being connected to the user interface and being responsive to actions by a user on said user interface, said control system being programmed to:
store a plurality of reference values defining a shaping profile,
store the value of at least a discriminating factor which relates to the time-varying parameter, the time-varying parameter being the net weight loss during a time interval and the discriminating factor value being the total weight loss to be achieved at the end of a total treatment time, and
calculate each of the parameter values as a function of a corresponding reference value of the shaping profile and of the value of said discriminating factor by:
multiplying the shaping profile reference values by the value of the total weight loss for obtaining a plurality of actual weight loss portions,
multiplying time interval values by the total treatment time value to obtain actual time intervals, and
associating each actual weight loss portion with the respective actual time interval during which the actual weight loss portion is achieved.

48. A blood treatment according to claim 47, wherein the control system is further programmed to:
   store a plurality of shaping profiles to form a shaping profiles library, allowing selection from the shaping profiles library of any of said shaping profiles, and to calculate the parameter values starting from reference values of the selected shaping profile.

49. A blood treatment according to claim 47, wherein the control system is programmed to allow the user to set said discriminating factor value.

50. A blood treatment apparatus according to claim 47, wherein the control system is programmed to check a sum of the reference values and to generate an error signal if the sum is higher than a reference threshold value.

51. A blood treatment apparatus according to claim 47, wherein the shaping profile includes a plurality of time interval value, and wherein the control system is programmed to check a sum of the time interval values and to generate an error signal if the sum is higher than a reference threshold value.

* * * * *